(12) United States Patent
Keisari et al.

(10) Patent No.: US 7,395,112 B2
(45) Date of Patent: Jul. 1, 2008

(54) METHOD AND APPARATUS FOR TREATING TUMORS USING LOW STRENGTH ELECTRIC FIELDS

(75) Inventors: Yona Keisari, Ramat Gan (IL); Rafi Korenstein, Rechovot (IL); Igor Entin, San Francisco, CA (US); Yosef Rosemberg, Ra'anana (IL)

(73) Assignee: Ramot At Tel Aviv University Ltd., Tel-Aviv (IL)

( * ) Notice: Subject to any disclaimer, the term of this patent is extended or adjusted under 35 U.S.C. 154(b) by 624 days.

(21) Appl. No.: 10/478,207

(22) PCT Filed: Jun. 9, 2002

(86) PCT No.: PCT/IL02/00445

§ 371 (c)(1),
(2), (4) Date: Nov. 28, 2003

(87) PCT Pub. No.: WO02/098501

PCT Pub. Date: Dec. 12, 2002

(65) Prior Publication Data

US 2004/0158288 A1  Aug. 12, 2004

(51) Int. Cl.
*A61N 1/00* (2006.01)
(52) U.S. Cl. .......................................................... 607/3
(58) Field of Classification Search .................... 607/2, 607/3, 115, 116; 604/21
See application file for complete search history.

(56) References Cited

U.S. PATENT DOCUMENTS 6,241,701 B1 *  6/2001  Hofmann ...................... 604/21

OTHER PUBLICATIONS

J. Belechradek, Jr. et al. Electrochemotherapy of Spontaneous Mammary Tumours in Mice (1991).

(Continued)

*Primary Examiner*—Scott M. Getzow

(57) ABSTRACT

A method of treating tumor tissue of an individual is provided. The method is effected by applying to cells of the tumor tissue electrical field pulses having a strength, a repetition frequency and a pulse width selected capable of inducing endocytosis mediated cell death thereby treating the tumor tissue.

12 Claims, 21 Drawing Sheets

OTHER PUBLICATIONS

Maurice Chazal, et al. Treatment of hapatic metastases of colorectal cancer by electrochemotherapy: An experimental study in the rat. (1998).

L. Frank Glass, et al. Bleomycin-Mediated Electrochemotherapy of Metastatic Melanoma. (1996).

L. Frank Glass, et al. Bleomycin-mediated electrochemotherapy of basal cell carcinoma. (1996).

R. Heller, et al. Effective treatment of B16 melanoma by direct delivery of bleomycin using electrochemotherapy. (1997).

Richard Heller, et al. Phase I/II Trial for the Treatment of Cutaneous and Subcutaneous Tumors Using Electrochemotherapy. (1995).

Richard Heller, et al. Treatment of Cutaneous and Subcutaneous Tumors with Electrochemotherapy Using Intralesional Bleomycin. (1998).

Mark J. Jaroszeski, et al. In vivo antitumor effects of electrochemotherapy in a hepatoma model. (1996).

Yoko Kubota, et al. Histological Evaluation of the Effects of Electropermeabilization after Administration of Bleomycin on Bladder Cancer in the Rat. (1998).

Yoko Kubota, et al. Successful Treatment of Metastatic Skin Lesions with Electrochemotherapy. (1998).

Yoko Kubota, et al. Electropermeabilization in bladder cancer chemotherapy. (1996).

LM Mir, et al. Effective treatment of cutaneous and subcutaneous malignant tumours by electrochemotherapy. (1998).

Yosef Rosemberg, et al. Incorporation of macromolecules into cells and vesicles b low electric fields: induction of endocytotic-like processes. (1997).

Gregor Sersa, et al. Anti-tumor effectiveness of electrochemotherapy with bleomycin is increased by TNF-$\alpha$ on SA-1 tumors in mice. (1997).

Gregor Sersa, et al. Antitumor Effectiveness of Electrochemotherapy with cis-diamminedichlorlplatinum (II) in Mice. (1995).

Mark J. Jaroszeski, et al. Electrochemotherapy, Electrogenetherapy, and Transdermal Drug Delivery.

Michael Belehradek, M.D.et al. Electrochemotherapy, a New Antitumor Treatment. (1993).

Micheline Hyacinthe, M.D., et al. Electrically Enhanced Drug Delivery for the Treatment of Soft Tissue Sarcoma. (1998).

M.J. Jaroszeski, et al. Treatment of hepatocellular carcinoma in a rat model using electrochemotherapy. (2000).

Shigeki Kuriyama, M.D. et al. Electrochemotherapy for Colorectal Cancer with Commonly Used chemotherapeutic Agents in a Mouse Model. (2000).

Gregory Sersa, et al. Electrochemotherapy with Cisplatin: Clinical Experience in Malignant Melanoma Patients. (1999).

G. Sersa, et al. Electrochemotherapy with Cisplatin: Potentiation of Local Cisplatin Antitumour Effectiveness by Application of Electric Pulses in Cancer Patients. (1998).

Sergio Rodriguez-Cuevas, et al. Electrochemotherapy in Primary and Metastatic Skin Tumors: Phase II Trial Using Intralesional Bleomycin. (2001).

M. Cemazar, et al. Electrochemotherapy of tumours resistant to cisplatin: a study in a murine tumour model. (2001).

M. Cemazar, et al. Electroporation of human microvascular endothelial cells: evidence for an anti-vascular mechanism of electrochemotherapy. (2000).

Akiko Horiuchi, et al. Enhancement of Antitumor Effect of Bleomycin By Low-Voltage In Vivo Electroporation: A Study of Human Uterine Leiomyosarcomas in Nude Mice. (2000).

* cited by examiner

| | LEF. 20V/cm | LEF. 40V/cm | LEF. 60V/cm | LEF. 70V/cm |
|---|---|---|---|---|
| TB mice | 0.00027 | 0.00063 | 0.00023 | 0.00000 |
| LEF. 40V/cm | 0.21 | | | |
| LEF. 60V/cm | 0.0042 | 0.01 | | |
| LEF. 70V/cm | 0.00014 | 0.00056 | 0.77 | |

|  | TB mice | BLM. | LEF (40V/cm, 12 min) | BLM-LEF (40V/cm, 12 min) | LEF (20V/cm, 12 min) | LEF (20V/cm, 20 min) |
|---|---|---|---|---|---|---|
| BLM | 0.02 | | | | | |
| LEF (40V/cm, 12 min) | 0.35 | 0.66 | | | | |
| BLM-LEF (40V/cm, 12 min) | 0.00008 | 0.0002 | 0.0002 | | | |
| LEF (20V/cm, 12 min) | 0.51 | 0.69 | 0.62 | | | |
| BLM-LEF (20V/cm, 12 min) | 0.00014 | 0.006 | | 0.14 | 0.67 | |
| LEF (20V/cm, 20 min) | 0.11 | 0.98 | 0.85 | | 0.67 | |
| BLM-LEF (20V/cm, 20 min) | 0.00086 | 0.017 | | 0.19 | | 0.0099 |

Fig. 4c

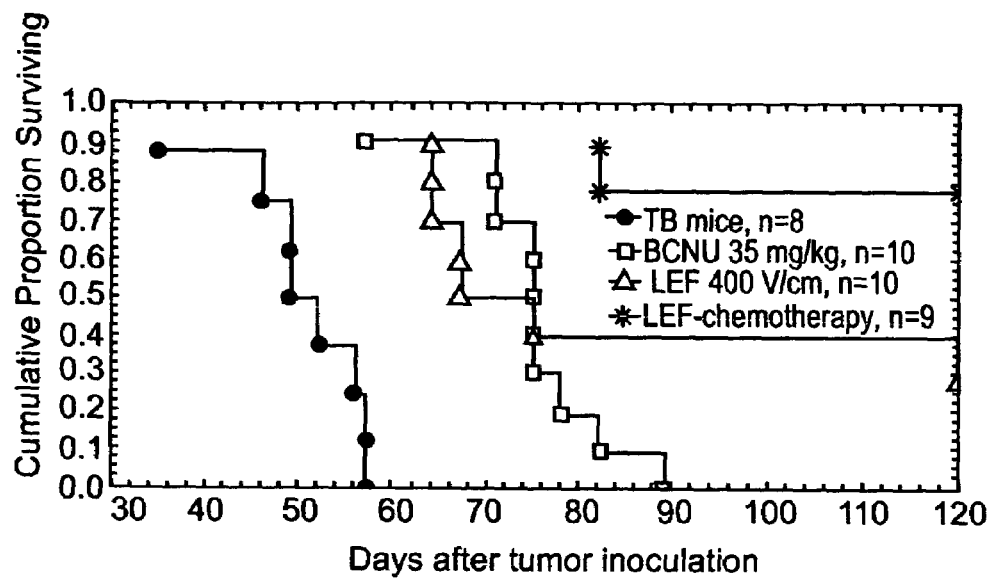
Fig. 11a
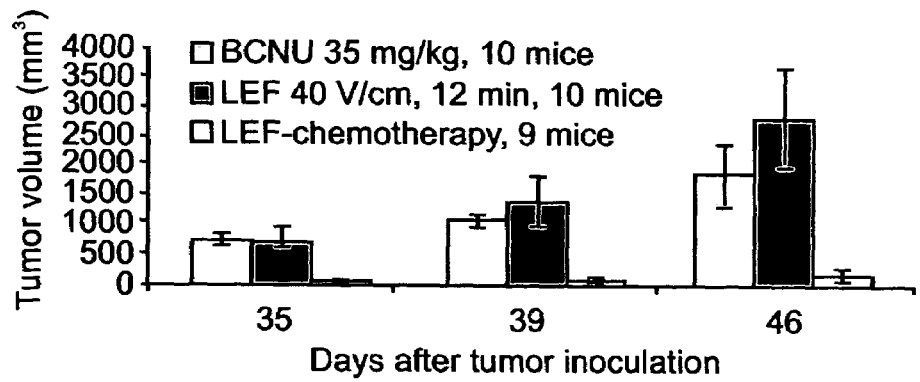
Fig. 11b
|  | BCNU (35 mg/kg) vs. | LEF (40 V/cm) vs. | LEF chemotherapy vs. |
|---|---|---|---|
| TB mice | 0.0003 | 0.00001 | 0.00002 |
| LEF 40V/cm | 0.31 | | |
| LEF chemotherapy | 0.00008 | 0.022 | |
Fig. 11c

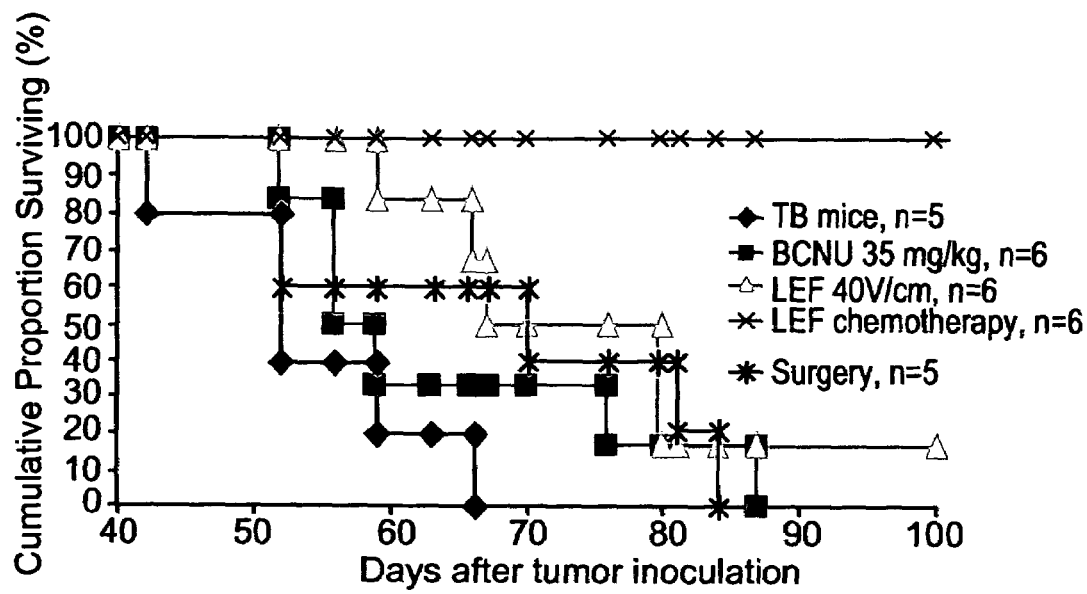
Fig. 12a
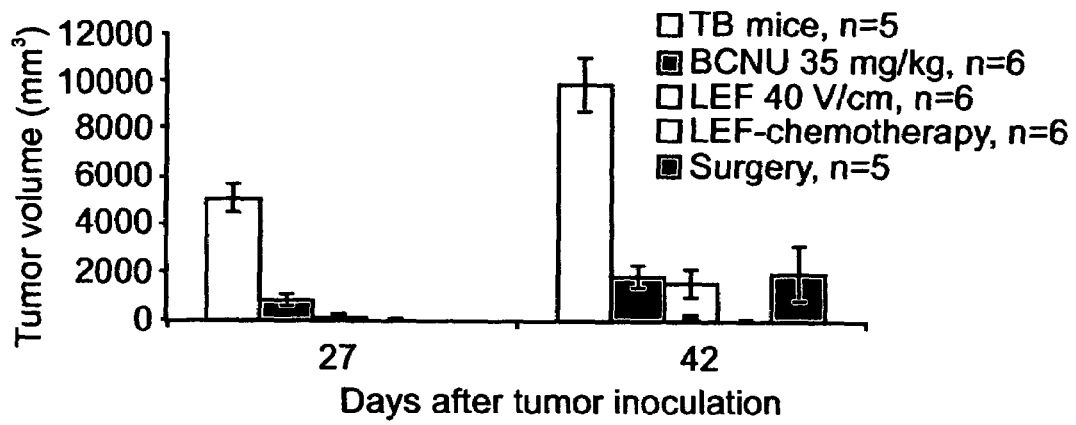
Fig. 12b
|  | BCNU 35 mg/kg | LEF 40 V/cm | Surgery |
|---|---|---|---|
| TB mice | 0.21 | 0.0083 | 0.068 |
| LEF 40V/cm | 0.2 |  |  |
| Surgery | 0.9 | 0.74 |  |
Fig. 12c

METHOD AND APPARATUS FOR TREATING TUMORS USING LOW STRENGTH ELECTRIC FIELDS

FIELD AND BACKGROUND OF THE INVENTION

The present invention relates to methods of using low-strength electric fields to treat tumors. More particularly, the present invention relates to methods and an apparatus which utilize low strength pulsed electric fields on the order of 20-70 V/cm, with or without adjunct chemotherapy to treat or cure various tumor and cancerous tissue.

Cancer is second only to heart disease as a cause of death, accounting for 22% of all deaths (Fraumeni J F, Devesa S S, Hoover R N, Kinlien L J. Epidemiology of cancer. In: Cancer—principles and practice of oncology, DeVita V T, Hellman S, Rozenberg S A, (eds.) pp. 150, Lippincott J. R. Co., Philadelphia, 1993. Colon cancer, melanoma and breast cancer are three particularly problematic types of cancer.

Melanomas are aggressive, frequently metastatic tumors derived from either melanocytes or melanocyte related nevus cells ("Cellular and Molecular Immunology" (1991) (eds) Abbas A. K., Lechtman, A. H., Pober, J. S.; W.B. Saunders Company, Philadelphia: pages 340-341) which make up approximately 3% of all skin cancers. Of particular concern is the current worldwide increase in melanoma which is unsurpassed by any other neoplasm with the exception of lung cancer in women ("Cellular and Molecular Immunology" (1991) (eds) Abbas, A. K., Lechtiman, A. H., Pober, J. S.; W.B. Saunders Company Philadelphia pages: 340-342; Kirkwood and Agarwala (1993) Principles and Practice of Oncology 7:1-16). The aggressiveness of melanoma is such that even when melanoma is apparently localized to the skin, up to 30% of the patients will develop systemic metastasis and the majority will die.

Breast cancer is a significant health problem for women in the United States and throughout the world. Although advances have been made in detection and treatment of the disease breast cancer remains the second leading cause of cancer-related deaths in women, affecting more than 180,000 women in the United States each year. For women in North America, the life-time odds of getting breast cancer are now one in eight.

Colon cancer is the second most frequently diagnosed malignancy in the United States as well as the second most common cause of cancer death. About 100,000 new cases of colon cancer are diagnosed yearly, with about 50,000 deaths. The five-year survival rate for patients with colorectal cancer detected in an early localized stage is 92%; unfortunately, only 37% of colorectal cancer is diagnosed at this stage. The survival rate drops to 64% if the cancer is allowed to spread to adjacent organs or lymph nodes, and to 7% in patients with distant metastases. Recurrence following surgery (the most common form of therapy) is a major problem and is often the ultimate cause of death. In spite of considerable research into therapies for the disease, colon cancer remains difficult to diagnose and treat.

The leading cause of cancer death in general is due to growth of metastases since, in the majority of cases, by the time a malignancy has been diagnosed, metastases have already spread to other sites (for review see Fidler and Balch, 1987. Curr. Prob. Surg. 24:137). Whereas metastatic primary tumors can in many cases be surgically removed, greatly contributing to satisfactory therapeutic outcomes, metastases, such as disseminated micrometastases, can be difficult or impossible to locate and/or reach and thus surgical removal such metastases is usually not an option. Thus, metastases pose the most serious challenge to cancer therapy and are the main cause of failure of treatment of this disease. Therefore, prevention of metastasis is necessary to improve the prognosis of cancer patients.

In order to treat cancer effectively efficient removal of the primary tumor mass and prevention of secondary tumor growth, and eradication of metastatic cells must be achieved. Furthermore, significant prevention of recurrence of cancer growth can be achieved by generation of anti-cancer immune responses.

Surgical excision of tumors is the most widely employed therapeutic modality for the treatment of cancer, in which the primary goal is the complete eradication of local and regional tumor. This involves removal of adequate margins of normal tissue surrounding the tumor, and radical wide excision in order to prevent local recurrence. However, despite major advances in the surgical pre- and postoperative care of patients, surgical treatment of malignant neoplasms remains highly limited (Eilber F R. Principles of cancer surgery. In: Cancer Treatment, Haskell C M, (ed.) 5th ed., pp. 47, W.B. Saunders Co. Philadelphia, 2001). Surgical techniques are effective only in the area of the primary tumor or regional lymphatics and do not affect neoplasms located outside the operative field. Furthermore, due to anatomic location, many tumors cannot be treated by surgical resection because removal of an adequate margin of normal tissue cannot be achieved. Also, surgical treatment is often not an option for tumors intimately involving major blood vessels or essential organs. As well, many patient present problematic medical histories, such as cerebrovascular or cardiovascular accidents, or uncontrolled diabetes, rendering them poor surgical candidates because of their high postoperative mortality rate. Also, in many cases, tumor excision can not performed without causing unacceptable levels of impairment of physiologic functions or cosmetic damage.

Chemotherapy alone or in combination with surgery is commonly the most efficient anti-cancer remedy (Haskell C M. Principles of cancer chemotherapy. In: Cancer Treatment, Haskell C M, (ed.) 5th ed. pp. 62-86, W.B. Saunders Co. Philadelphia, 2001). However, chemotherapeutic agents often cause severe and unacceptable side-effects, such as bone marrow and lymphoid organ damage resulting in immunosuppression, thereby rendering subjects highly vulnerable to lethal opportunistic infections, as well as various other types of organ toxicities. Thus, the use of cytotoxic drugs is limited only to tolerated doses. One way to reduce minimal therapeutic doses of chemotherapeutic agents would be to enhance the efficiency of uptake of chemotherapeutic drugs into cancer cells.

During the last two decades, various techniques based on biological, chemical and physical processes have been developed for facilitating incorporation of macromolecules into cells. Methods for intracellular delivery of exogenous substances based on biological phenomena have employed molecules controlling the activity of specific membrane channels in various cell types (Heppel and Weisman, 1985. J Membr Biol. 86:189), pore-forming toxins (Ahnert-Higler et al., 1989. Methods Cell Biology 31:63) and liposome-endocytosis mediated delivery of compounds (Friend et al., 1996. Biophys Acta 1278:41). Some permeabilization methods are based on chemical modification of cell membranes by various substances, most commonly via the use of detergents as permeabilizing agents. Other methods based on chemically induced permeabilization include protease digestion or stimulation of DNA binding to the cell surface by formation of neutral complexes of DNA with various molecules. Physical methods of introducing molecules into cells include application of hypotonic stress (Poulin et al., 1993. J Biol Chem. 268:4690), cell bombardment by coated molecules (Salford et al., 1993a), microinjection (Soreg and Seidman, 1992. Methods Enzymol. 207:225), electroporation (Potter, 1993. Methods Enzymol. 217:461), and exposure to pulsed low electric fields (LEFs) (Rosenberg and Korenstein, 1997. Bioelectrochemistry and Bioenergetics 42:275).

Electroporation involves formation of a reversible, high permeability plasma membrane state in cells or bacteria exposed to 50-200 μs pulses of high-strength electric fields in the range of 500-5000 V/cm. At a threshold value of about 1 V across the cell membrane, a sudden increase in membrane permeability is observed which is thought to be mediated by stabilization of transient membrane defects and to their expansion to large metastable hydrophilic pores. Both transient and stable pores can be the sites of extrinsic material entry into the cell (Hapala, 1997. Crit Rev Biotechnol. 17:105; Rols and Teissie, 1990. Biophys J. 58:1089; Rols and Teissie, 1998. Biophys J. 75:1415). Electroporation also appears to involve stimulation of biological endocytosis in areas of destabilized membrane structure (Rols et al., 1995. Biochem Biophys Acta 1111:45). While electroporation, also termed electropermeabilization or electroinjection, has been generally used as a method of transfecting cells with nucleic acids, this method has also been used to load cells with a variety of other molecules, including proteins (Lambert et al., 1990. Biochem Cell Biol. 68:729), such as phalloidin (Hashimoto et al., 1989. J Biochem Biophys Methods 19:143) or antibodies (Chakrabarti et al., 1989. J Biol Chem. 264:15494).

In contrast to electroporation, incorporation of macromolecules into cells via exposure to LEFs, a methodology developed by the present inventors, utilizes low voltage electric fields. Exposure of cells and vesicles to LEFs leads to efficient intracellular incorporation of various molecules, including carbohydrates, such as polysaccharides, and proteins, such as β-galactosidase (Rosenberg and Korenstein, 1997. Bioelectrochemistry and Bioenergetics 42:275) via an underlying mechanism involving endocytosis-like processes. Exposure of membrane vesicles and cells to such LEFs leads to electrophoretic lateral mobility of charged proteins and lipids in the plane of the cell membrane (Poo, 1981. Bioeng. 10:245; Brumfield et al., 1989 Biophys J. 56:607), and generation of transmembrane potential differences (Farkas et al., 1984. Biophys J. 45:363). It has been shown by the present inventors that exposure of cells in suspension or monolayer to trains of pulsed unipolar electric fields in the range of about 1-100 V/cm (Rosenberg and Korenstein, 1997. Bioelectrochemistry and Bioenergetics 42:275), or to AC fields with peak-to-peak amplitudes of about 1-60 V/cm leads to efficient uptake of macromolecules having molecular weights ranging from about 1 to 2000 kDa, an exceptionally broad range. Unlike following electroporation, cells exposed to LEFs in vitro maintain high viability due to the magnitudes of the applied electric fields being too low to induce changes in membrane permeability via physical disruption of its integrity (Rosenberg and Korenstein, 1990. Biophys J. 58:823). LEFs have been shown to induce endocytosis, a process which includes a complex sequence of membrane-linked processes resulting in uptake of extrinsic substances involving binding of such substances to the cell surface, formation of endocytotic vesicles and maturation of endocytotic vesicles to lysosomes (Mellman, 1996. Ann Rev Cell Dev Biol. 12:575).

Several prior art approaches employing electric fields have been employed to treat tumors.

One approach has employed electroporation in conjunction with netropsin, bleomycin, or melphalan to attempt to increase of the cytotoxicity of these drugs against cultured DC-3F cells (Orlowski S. et al., 1988. Biochem Pharmacol. 37:4727).

Yet an additional approach has utilized electroporation in conjunction with daunorubicin, doxorubicin, etoposide, paclitaxel, carboplatin or cisplatin in order to attempt to potentiate their cytotoxic effect against cultured cells (Gehl J. et al., 1998. Anticancer Drugs 9:319).

Still another approach has employed very high strength electric field electroporation (1,300 V/cm) in conjunction with administration of cis-diamminedichloroplatinum (II) in order to attempt to treat SA-1, EAT, or B16 melanoma tumors in mice (Sersa G. et al., 1995. Cancer Res. 55:3450)

An additional approach has used electroporation in conjunction with administration of bleomycin in order to attempt to treat tumors of the female genital squamous cell carcinoma cell line CaSki in nude mice (Yabushita H. et al., 1997. Gynecol Oncol. 65:297).

Another approach has used very high strength electric field electroporation (1,300 V/cm) in conjunction with administration of bleomycin to attempt to treat head and neck squamous cell carcinoma (Belehradek J J. et al., 1993. Cancer 72:3694).

Yet another approach has utilized very high strength electric field electroporation (1,000-1,300 V/cm) in conjunction with administration of bleomycin to attempt to treat head and neck squamous cell carcinoma, and salivary and breast adenocarcinomas (Domenge C. et al., 1996. Cancer 77:956) However, all of the aforementioned prior art approaches suffer from significant disadvantages.

For example, all of these prior art approaches have employed electroporation, and hence high-strength electrical fields which, as described hereinabove, are significantly cytotoxic and which, by their extreme nature, are inherently hazardous. Electroporation suffers from the drawbacks of being inefficient in its potentiation of drug uptake, and in being restricted with respect to the range of molecular weights of the molecules whose uptake it is capable of potentiating. Prior art approaches have demonstrated potentiation of the in vivo anti-tumor effect of a restricted number of chemotherapeutic drugs (bleomycin, cisplatin, adriamycin and 5-fluorouracil). Moreover, none of these prior art methods has been shown to be effective in curing cancer at a metastatic stage. Critically, none of these prior art approaches has been shown to be effective against tumor cells in the absence of chemotherapeutic agents. Also none of these prior art approaches has demonstrated the capacity to upregulate anti-tumor immune responses as demonstrated by resistance to challenge.

Thus, all prior art approaches have failed to provide an adequate solution for treating tumors using electrical fields.

There is thus a widely recognized need for, and it would be highly advantageous to have, a method and apparatus devoid of the above limitation.

SUMMARY OF THE INVENTION

According to one aspect of the present invention there is provided a method of treating an individual having a neoplastic tumor, the method comprising applying to cells of the tumor electrical field pulses of a strength, a repetition frequency and a pulse width sufficient to induce endocytosis mediated cell death, thereby treating the individual.

According to another aspect of the present invention there is provided a method of treating an individual having a neoplastic pathology comprising applying to cells of a tumor electrical field pulses having a strength of 2-150 V/cm, a repetition frequency of 1 Hz-100 kHz and a pulse width of 1 µs-100 ms for a time period of 1 second to 60 minutes thereby treating the individual suffering from a neoplastic disorder.

According to yet another aspect of the present invention there is provided a method of treating an individual having a neoplastic and potentially metastatic tumor, the method comprising applying to cells of the tumor electrical field pulses of a strength, a repetition frequency and a pulse width sufficient to induce endocytosis mediated cell death thereby initiating or enhancing immune response to the cells in the individual, thereby treating the individual.

According to further features in preferred embodiments of the invention described below, the electrical field pulses are unipolar and are of a strength of 10-70 V/cm, a repetition frequency of 100 Hz-10 kHz and a pulse width of 1-200 µs.

According to still further features in the described preferred embodiments the method further comprising exposing the cells of the tumor to a cytotoxic agent concomitant or prior to application of the electrical field pulses.

According to still further features in the described preferred embodiments the exposing the cells of the tumor to the cytotoxic agent is effected 0.1-20 minutes prior to the application of the electrical field pulses.

According to still further features in the described preferred embodiments the electrical field pulses are unipolar and are of a strength of 10-40 V/cm a repetition frequency of 300-2000 Hz and a pulse width of 1-200 µs.

According to still further features in the described preferred embodiments the exposing the cells of the tumor to the cytotoxic agent is effected by administering the cytotoxic agent to the individual.

According to still further features in the described preferred embodiments the administering is effected by directly injecting the cytotoxic agent into or around the tumor.

According to still further features in the described preferred embodiments the cytotoxic agent is selected from the group consisting of bleomycin, 5-fluorouracil, cisplatin, taxol, doxorubicin, cyclophosphamide, methotraxate and carmustine.

According to still further features in the described preferred embodiments the cytotoxic agent is provided in a carrier mixture including oleum ricini and ethanol.

According to still further features in the described preferred embodiments the method further comprising determining a volume of the tumor, the volume being for determining the strength, repetition frequency and the pulse of the electrical field pulses applied to the cells of the tumor.

According to still further features in the described preferred embodiments the applying to cells of the tumor the electrical field pulses is effected in the absence of a cytotoxic agent.

According to still further features in the described preferred embodiments the neoplastic pathology is a sarcoma or carcinoma, selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, broncliogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma and neuroblastoma.

According to still another aspect of the present invention there is provided an apparatus for treating an individual suffering from a neoplastic pathology comprising: (a) an electrode system including an anode electrode and at least one cathode electrode configured for placement in contact with a tissue of the individual; (b) a power source being in circuit communication with the electrode system and being for generating an electrical potential across the electrode system; and (c) a controller being for setting the duration, frequency and strength of the electrical potential in a manner enabling the electrode system placed within the tissue to expose cells of the tissue to electrical field pulses having a strength of 2-150 V/cm, a repetition frequency of 1 Hz-100 kHz and a pulse width of 1 µs-100 ms for a time period of 1 second to 60 minutes.

According to still further features in the described preferred embodiments the controller enables setting of the strength of the electrical potential in increments of 1 mV.

According to still further features in the described preferred embodiments the electrode system includes three cathode electrodes.

According to still further features in the described preferred embodiments the anode electrode and the at least one cathode electrode are needle electrodes.

According to still further features in the described preferred embodiments the electrode system includes a support for holding the anode electrode and the cathode electrodes and for simultaneously contacting the anode electrode and the cathode electrodes with the tissue region.

According to still further features in the described preferred embodiments the anode electrode and the cathode electrodes are held by the support in a configuration which enables placement of the anode electrode in a center of the tissue and the cathode electrodes in a periphery of the tissue.

According to still further features in the described preferred embodiments the apparatus further comprising a processing unit being connected to the controller, the processing unit being for determining the duration, the frequency and the strength of the electrical potential according to an input of a volume of the tissue region.

According to still further features in the described preferred embodiments the apparatus further comprising an injector mechanism for injecting a cytotoxic agent into the tissue.

According to still further features in the described preferred embodiments the injector mechanism forms a part of the electrode system.

According to still further features in the described preferred embodiments the injector mechanism is at least partially integrated within the anode cathode.

According to an additional aspect of the present invention there is provided a method of stimulating an individual's immune response to tumor cell, the method comprising applying to cells of a tumor tissue electrical field pulses of a strength, a repetition frequency and a pulse width sufficient to stimulate an individual's immune response to the cells.

According to still further features in the described preferred embodiments the applying to cells of the tumor tissue the electrical field pulses is effected in the absence of a cytotoxic agent.

According to still further features in the described preferred embodiments the applying to cells of the tumor tissue the electrical field pulses is effected in the presence of an administered immunostimulatory agent.

According to still further features in the described preferred embodiments the immunostimulatory agent is composed of a mixture of oleum ricini and ethanol.

The present invention successfully addresses the shortcomings of the presently known configurations by providing an apparatus and method highly effective in treating an individual having a neoplastic disorder such as cancer.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard. no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a is a data plot depicting cumulative survival of CT-26 tumor bearing mice. Untreated tumor bearing mice (TB). FIG. 1b is a table depicting statistical analysis of results obtained.

FIGS. 4a-c depict the effect of various combinations of LEF/bleomycin treatments on CT-26 tumor progression. FIGS. 4a and 4b are data plots respectively depicting percent survival of tumor bearing mice treated with the indicated combinations of LEF and bleomycin (chemotherapy) treatments. FIG. 4c is a table depicting statistical analysis of the results obtained in FIGS. 4a and 4b.

FIGS. 11a-c depict results from treatment of mice bearing 10 mm diameter CT-26 tumors via BCNU, LEF alone or LEF with BCNU. FIGS. 11a-b are a data plot depicting survival and a histogram depicting tumor size, respectively, and FIG. 11c is a table depicting statistical analysis of results obtained in FIG. 11a. TB mice—untreated tumor-bearing mice, BCNU 35 mg/kg—tumor bearing mice treated with BCNU (35 mg/kg) only, LEF 40 V/cm—tumor bearing mice treated with LEF (40 V/cm, 12 min) only, LEF-chemotherapy—tumor bearing mice treated with LEF (40 V/cm, 12 min) with BCNU (35 mg/kg).

FIGS. 12a-c depict results from treatment of mice bearing 15 mm diameter CT-26 tumors via BCNU, LEF alone, LEF with BCNU, or surgery. FIGS. 12a-b are a data plot depicting survival and a histogram depicting tumor size, respectively, and FIG. 12c is a table depicting statistical analysis of results obtained in FIG. 12a. TB mice—untreated tumor-bearing mice, BCNU 35 mg/kg—tumor bearing mice treated with BCNU (35 mg/kg) only, LEF 40 V/cm—tumor bearing mice treated with LEF (40 V/cm, 12 min) only, LEF-chemotherapy—tumor bearing mice treated with LEF (40 V/cm, 12 min) with BCNU (35 mg/kg), Surgery—tumor bearing mice treated with surgery only.

DESCRIPTION OF THE PREFERRED EMBODIMENTS

Figures 1A, 1B:
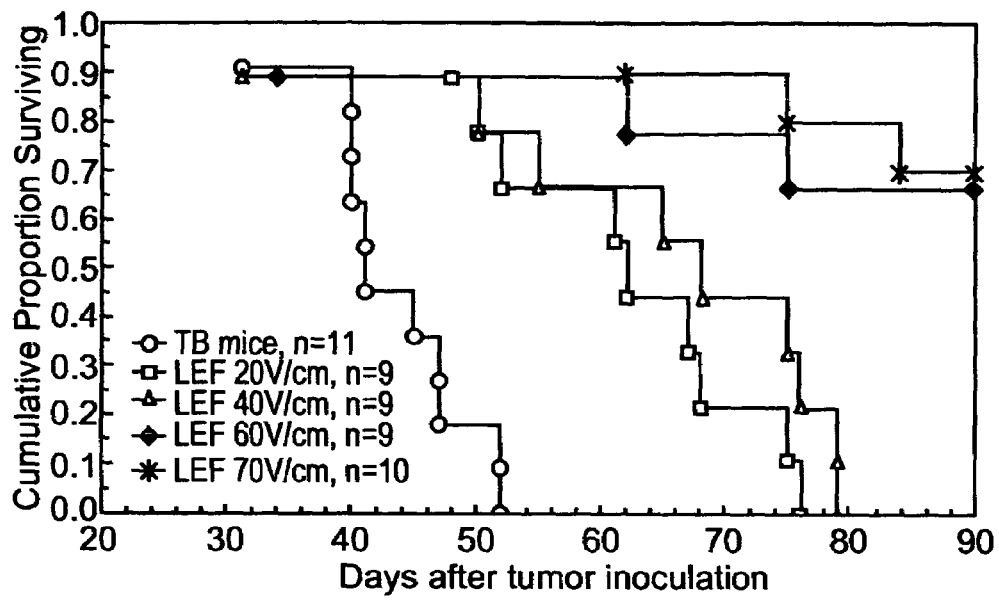
FIGS. 1a-b depict the effect of LEF treatment alone on survival of CT-26 tumor bearing mice.

The present invention is of a method and apparatus which can be used to treat tumors. Specifically, the present invention can be used to treat tumors by exposing tumor cells to a low electric field of a distinct parameter in the presence or absence of cytotoxic drugs.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Numerous cancer treatment modalities are known in the art including various surgical procedures and/or treatments utilizing various cytotoxic drugs.

In attempts to increase the efficacy of cytotoxic drugs against tumor cells researchers have devised methodology for increasing the uptake and thus exposure of these cells to the cytotoxic drugs.

Thus, approaches such as electroporation have been used in conjunction with various cytotoxic drugs in order to attempt to potentiate their cytotoxic effect against tumor cells.

Incorporation of molecules into cells via exposure to low electric fields (LEFs), a methodology developed by the present inventors (U.S. Pat. No. 5,964,726) has also been used to introduce cytotoxins into tumor cells.

The use of low strength electric field therapy provides numerous benefits including, but not limited to, very high efficiency of incorporation of molecules, including macromolecules into treated cells, resulting in intracellular concentrations of cytotoxins that are at least several fold higher than their extracellular concentration, potent and specific adjunct anti-tumor activity intrinsic to the LEF itself, and generation of subsequent immunoprotection from re-growth of cured tumors.

In the present study, the present inventors have experimented with various electrical pulse parameters in efforts of improving the therapeutic efficiency of the LEF approach.

As illustrated in the Examples section which follows, the present study uncovered that an electrical pulse of a distinct signature range (as characterized by parameters of strength, duration and frequency) substantially improves the efficacy of cytotoxic agents in treating tumors as compared to prior art electroporation based approaches. Unexpectedly, the present inventors have also uncovered that an electrical pulse of another distinct signature range can be used to treat tumors without having to utilize cytotoxic agents.

Thus, according to one aspect of the present invention there is provided a method of treating an individual suffering from a neoplastic disorder such as for example, cancer.

As used herein, the phrase "neoplastic pathology" refers to any disorder characterized by formation of tissue which includes cells exhibiting abnormal growth (e.g., hyperproliferation) or phenotype; such tissue is also referred to herein as a "tumor". Cancer such as sarcoma or carcinomas or any other hyperproliferative disorders are considered herein as neoplastic pathologies.

As used herein, the term "treating" when used in conjunction with a tumor refers to halting growth of the tumor tissue, reducing its size or eradicating such tumor tissue.

The method according to this aspect of the present invention is effected by applying to cells of the tumor electrical field pulses having a strength of 2-150 V/cm, a repetition frequency of 1 Hz-100 kHz and a pulse width of 1 µs-100 ms for a time period of 1 second to 60 minutes. Preferably, the parameters are selected such that the average power applied to the cells of the tumor over the treatment period in the range of 1.4 mW-2.25 W.

Selection of appropriate pulse parameters is preferably effected with respect to the tumor size, type of chemotherapy (when utilized) and type of cells. Further description relating to selection of pulse parameters is provided in the Examples section which follows.

Depending on the location and size of the tumor, application of such electrical pulses can be effected using surgically positioned electrodes or preferably by using electrodes which can be directly inserted into the individuals body and positioned in or around the tumor. Further description relating to methodology and electrode configurations suitable for application of electrical field pulses to tumor tissue according to the teachings of the present invention is provided herein below and in the Examples section which follows.

Preferably, the electric pulses applied to the tissue are unipolar, although bipolar pulses can also be used with some embodiments of the present invention. Preferably, the electrical pulses are of a strength of 2-100 V/cm, a repetition frequency of 100 Hz-1 kHz and a pulse width of 1-200 μs, more preferably, the electrical pulses are of a strength of 5-80 V/cm, a repetition frequency of 200-800 Hz and a pulse width of 50-200 μs, most preferably, the electrical pulses are of a strength of 10-70 V/cm, a repetition frequency of 300-500 Hz and a pulse width of 100-200 μs.

As shown in the Examples section below, LEFs having a field strength of about 70 V/cm, a repetition frequency of about 500 Hz and a pulse width of 180 μs are effective in treating tumors.

Preferably, the electrical pulses are applied for a duration of 6-24 minutes, more preferably for a duration of 8-16 minutes and most preferably for a period of 10-14 minutes.

As demonstrated in the Examples section below, application of LEFs for a period of 12 minutes is particularly suitable for treating various types of tumors.

As described herein, the method of the present invention can be used with or with out administration of a cytotoxic agent.

When utilized in conjunction with a cytotoxic agent (low electric field enhanced cancer chemotherapy—LEFCT-EC) which can be administered prior to (preferably 0.1-20 minutes, more preferably 2-4 minutes) or concomitant with application of the electrical pulses, the method of the present invention preferably utilizes electrical field pulses which are unipolar and are of a strength of 10-40 V/cm a repetition frequency of 300-500 Hz and a pulse width of 10-200 μs.

Administration of the cytotoxic agent can be effected systemically (e.g., via intravenous or intramuscular injection) or preferably via direct injection of the cytotoxic agent into or around the tumor or via selective perfusion of the tumor as taught, for example, in Lejeune F J. et al., 2001. Surg Oncol Clin N Am. 10:821.

Examples of cytotoxic agents which can be used with this embodiment of the present method include, but are not limited to, altretamine, amifostine, aminoglutheimide, asparginase, bleomycin, busulfan, capecitabine, carboplatin, carmustine, chlorambucil, cisplatin, cladribine, cyclophosphamide, cytarabine, dacarbazine, dactinomycin, daunorubicin, dexamethasone, diethylstilbestrol, docetaxel, doxorubicin, epirubicin, estramustine, etoposide, floxuridine, fludarabine, fluorouracil, flutamide, gemcitabine, goserelin, hexamethylmelamine, hydroxyurea, idarubicin, ifosfamide, irinotecan, leucovorin, leuprolide, leucovorim, levamisole, lomustine, mechlorethamine, megestrol, melphalan, mercaptopurine, methotrexate, mitomycin, mitotane, mitoxanthrone, octreotide, paclitaxel, pentostatin, plicamycin, prednisone, procarbazine, streptozocin, tamoxifen, teniposide, thioguanine, thiotepa, topotecan, vinblastine, vincristine, vinorelbine. Such cytotoxins can be used in combination with the LEF methodology of the present invention to treat primary and/or metastatic tumors associated with a neoplastic disorder including, but are not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma and neuroblastoma As shown in the Examples section which follows, the present method was highly effective in increasing the efficacy of cytotoxic treatment.

Furthermore, as shown in the Examples section below, administration of a mixture of oleum ricini and ethanol alone in conjunction with LEF treatment according to the teachings of the present invention can be used to treat tumors such as mammary carcinoma.

The Examples section which follows also demonstrates that the method of the present invention can be used as a general method to dramatically potentiate the effect of a range of cytotoxic agents such as bleomycin, BCNU, 5-FU, cisplatin and taxol against various tumor types, including some of the most widespread and lethal cancer types known, such as, for example, colon carcinoma, melanoma and mammary carcinoma.

As mentioned hereinabove and described in the Examples section which follows, the present inventors have also provided conclusive evidence showing that the present methodology can also be used to treat tumor tissue in the absence of cytotoxic drug administration.

This embodiment of the method of the present invention is effected by applying to cells of neoplastic/tumor tissue electrical field pulses of a strength, a repetition frequency and a pulse width sufficient to induce endocytosis mediated death of said cells in the absence of administration of a cytotoxic agent.

Thus, contrary to the teachings of the prior art, tumor therapy is achieved by this embodiment of the present approach in the total absence of an administered cytotoxin. Traversing cytotoxin administration is enabled by the electrical pulse parameters employed by this embodiment of the present method, since such parameters induce endocytosis in tumor cells and thus lead to endocytosis mediated transport of extracellular ions and molecules into tumor cells, which transport is not affected by transport equilibriums. The resultant high intracellular concentration of these ions and/or molecules triggers mechanisms which lead to cell death.

Treatment of tumor tissue according to this embodiment of the present invention provides numerous benefits. Since such treatment forgoes the use of cytotoxic drugs it avoids the side effects caused by the toxicity of the cytotoxic drug, it enables treatment of individuals sensitive to cytotoxic drug therapy and it substantially reduces the cost associated with tumor therapy.

In addition, such treatment also maintains or enhances the immune response directed against the neoplastic tissue and in particular metastases formed from such tissue.

Treatment according to this embodiment of the present invention preferably utilizes electrical field pulses which are unipolar and are of a strength of 10-70 V/cm a repetition frequency of 300-500 Hz and a pulse width of 10-200 μs. Further detail regarding this treatment approach is provided in the Example section which follows.

Thus, the present invention provides methodology which can be used to safely and effectively treat tumors with or without adjunct administration of cytotoxic agents.

As is illustrated in the Examples section which follows, one distinct and important advantage of the present invention lies in its ability to induce or enhance the individual's immune response against tumor cells thus inducing or enhancing the body's ability to combat metastasizing cells of the tumor. Thus, in effect, the present invention restores the individuals immunoprotection against growth of tumors cells or induces a potent response against such cells.

This feature of the present invention is pivotal to effective treatment of cancer since, as is further detailed in the background section hereinabove, prior art methods of eradicating tumor tissue (e.g., surgical procedures) directly remove, or lead to the removal of tumor associated antigens from the body and as such does not lead to a subsequent immune response against tumor cells.

As is illustrated in the Examples section which follows, the present study clearly demonstrates that the present methodology is highly effective in initiating or enhancing the individual's immune response against tumor cells. This effect of the present method is magnified when cells of the tumor are exposed to an oleum ricini-ethanol mixture, which in effect, functions as an immunostimulatory agent.

To facilitate tumor tissue treatment, the present invention also provides an apparatus specifically designed and configured for application of the tumor tissue treatments proposed hereinabove to an individual.

It may be appreciated by one skilled in the art that an apparatus being "configured" to produce the above described electrical parameters in vivo implies that (i) the portion of the apparatus that comes in contact with body tissue or fluid is preferably made of biocompatible materials (e.g., platinum or stainless steel), (ii) the electrodes of the apparatus are capable of carrying the current required for generating the electrical pulse described hereinabove around living cells in vivo and in an electrolyte which may include the tissue being treated, interstitial fluid, injected material at the treatment site, material applied to the target tissue, and combinations of the foregoing, and (iii) the material composing such electrodes should have a sufficient electrochemical and mechanical properties such that it does not break down as a result of electrical treatment.

Additionally, electrodes being configured to be located against or in a selected portion of target tissue means that the shape, flexibility and material forming such electrodes are selected suitable for such a purpose. Moreover, it will be apparent to those skilled in the art that where an apparatus is configured to perform treatment in the presence or absence of a cytotoxic drug that such an apparatus may be used to perform either or both functions.

Figure 25:
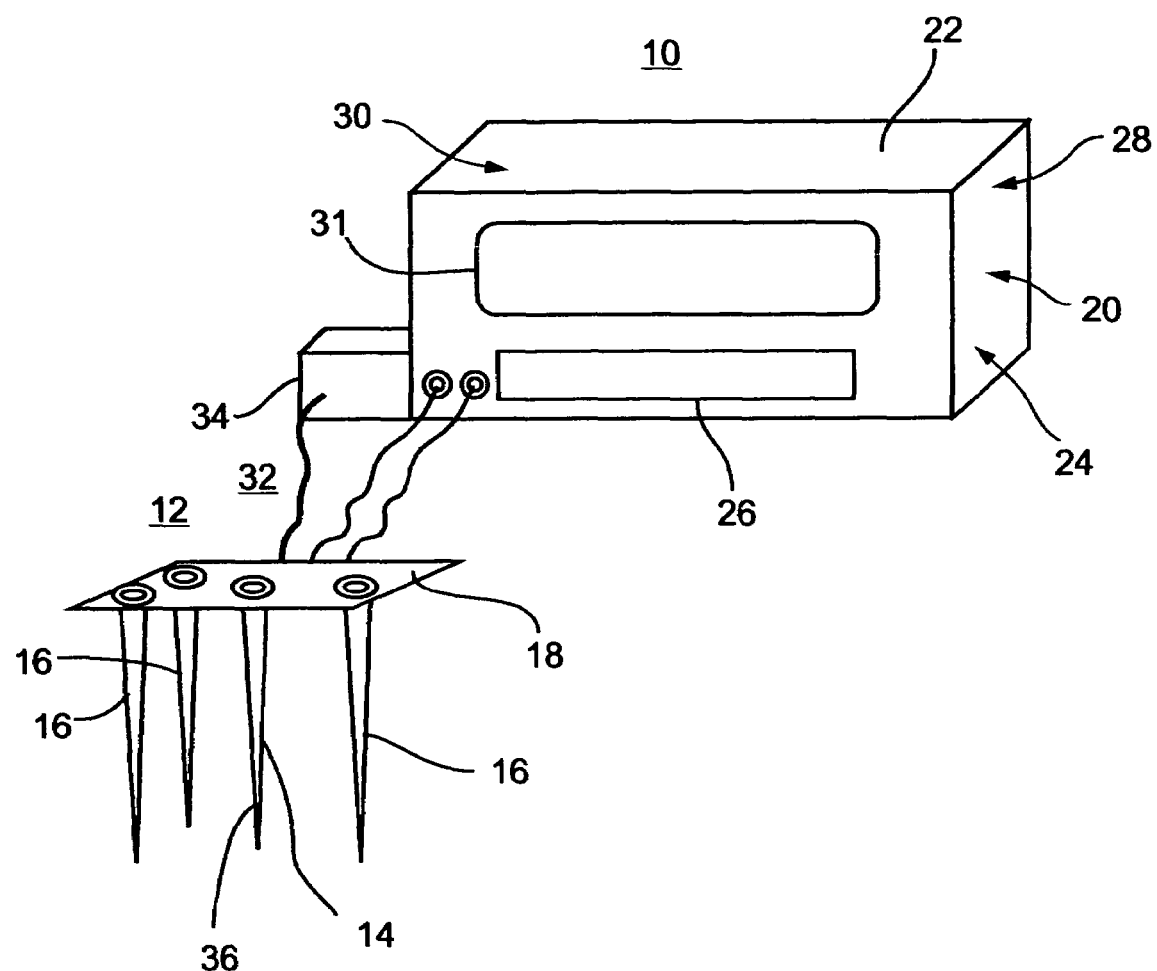
FIG. 25 illustrates a device suitable for treating tumor tissue according to the teachings of the present invention.

Referring now to the drawings, FIG. 25 illustrates an apparatus for treating an individual suffering from a neoplastic disorder which is referred to herein as apparatus 10.

Figure 15:
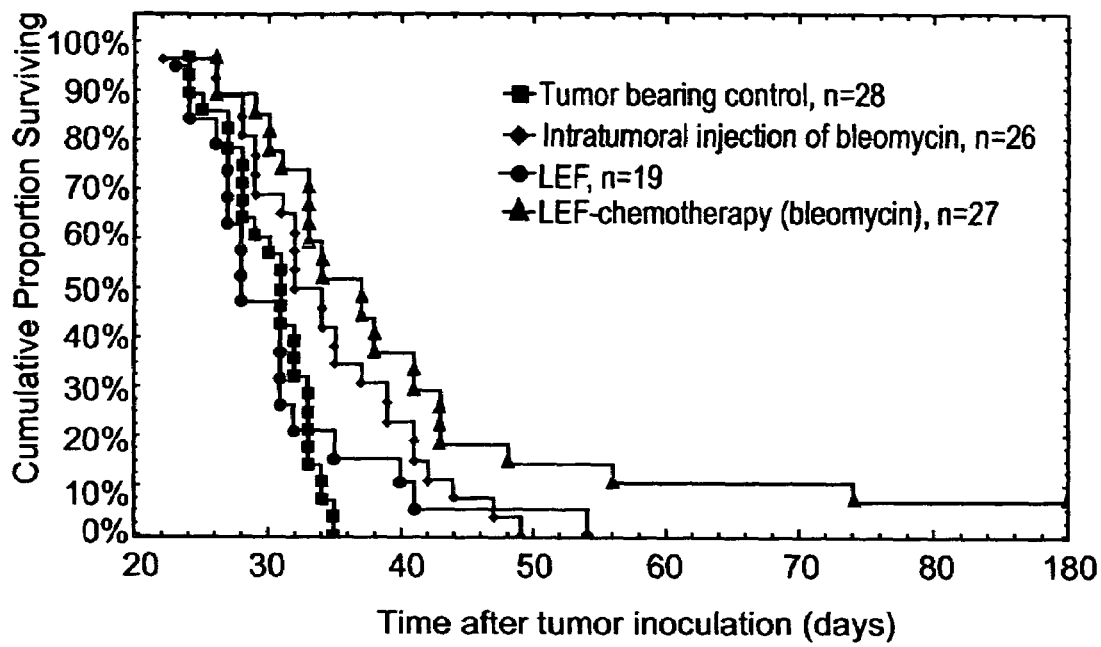
FIG. 15 is a data plot depicting cumulative survival of C57BL/6 mice bearing melanoma following LEFCT-EC with intratumoral bleomycin administration. Mice bearing melanoma were treated with bleomycin (8 U/kg) intratumorally and/or with LEF.

Apparatus 10 includes an electrode system 12 which includes a cathode electrode 14 and at least one anode electrode 16 (three are shown in FIG. 15), both being designed and configured for placement in contact with a tissue of the individual. Electrode system 12 preferably further includes a support 18 for holding electrodes 14 and 16 in an axially spaced apart configuration. Support 18 can be shaped as a plate and composed of, for example, plastic. Support 18 is preferably designed and configured to allow a user to configure the location of electrodes 14 and 16 thereupon in order to either achieve a particular electric field among the cells treated or to configure an electrode arrangement which accommodates a particular space or tissue configuration. Support 18 can hold any number of electrodes 14 and/or 16 in any configuration. FIG. 25 illustrates one such configuration wherein cathode electrode 14 is placed in the center of support 18 surrounded by three anode electrodes 16.

Electrodes 14 and 16 are preferably needle shaped and constructed of any suitable conductive material such as stainless steel, platinum, and other metals or alloys of metals. Electrodes 14 and 16 can also be covered with materials such as plastic in order to reduce the conductivity of the electrode or to change the direction of the field which is generated. Additionally, electrodes 14 and 16 can be easily removed from support 18 and discarded allowing for new electrodes to be placed thereupon, thereby making electrode system 12 suitable for uses requiring sterility and patient contact.

Electrode system 12 is in circuit communication with a power source 20 which is positioned within a housing 22 and which serves for producing a power; power source is preferably a 110-240 V AC input—AC or preferably DC output. The phrase "in circuit communication" as used herein is used to describe (i) devices that are directly or indirectly electrically connected with each other; (ii) devices having other devices or combinations of devices (e.g., breakers, relays, buffers, drivers, transmitters, receivers, and decoders) between them; (iii) devices in optical communication with each other (via, e.g., an optoisolator or fiber optic link); (iv) devices in electromagnetic communication with each other (via, e.g., radio frequency transmitter and receiver pair); (v) devices connected by and through other structures allowing them to communicate with each other; and (vi) any combination of any of the above.

Power source 20 serves for generating an electrical potential across electrode system 12. Power source 20 can include a pulse generator such as, for example, a PA-2000 or PA-4000 (both from Cyto Pulse Sciences, Inc., Columbia, Md.) or a T820, (BTX, Inc., San Diego, Calif.) modified to deliver LEF pulses of a predetermined shape, voltage, duration, and separation as described herein.

Apparatus 10 preferably further includes a controller 24 which serves for setting the duration, frequency and strength of electrical potential in a manner which enables electrode system 12 placed within the tissue treated to expose cells of the tissue to electrical field pulses having a strength of 5-100 V/cm, a repetition frequency of 100-700 Hz and a pulse width of 1-200 μs for a time period of 0.1 second to 60 minutes. Controller 24 can include components such as the PA-201 Programmable Pulse Switch or any other components suitable for enabling a user to set the desired pulse parameters. Preferably, controller 24 includes hardware/software for programming pulse parameters and is accurate and capable of setting electrical field parameters within 1 mV increments, the duration of the pulse in nanoseconds and the frequency of the pulse in 0.1 Hz increments.

Setting of controller 24 can be effected manually via a user input interface 26 by inputting the desired pulse parameters. A user can also input additional parameters relating to treatment such as the volume of tissue to be treated, the tissue type and the like. Furthermore, input interface 26 can also serve for inputting patient specific data such as patient ID, age, weight, treatment history and the like. The data entered is preferably saved to a magnetic, optical or optical-magnetic storage device 28 of apparatus 10.

Apparatus 10 preferably further includes a processing unit 30 which serves for determining duration, frequency and strength of electrical potential according to an input from the user of information relating to a volume of tissue to be treated, a tissue type or the like.

Apparatus 10 also includes an output interface 31 (e.g., display) which enables an operator to monitor treatment progress. Treatment progress can be monitored using feedback electrodes which form a part of electrode system 12 (e.g., integrated with electrodes 14 and 16). Feedback electrodes are designed to monitor the electrical state of the tissue treated and relay such monitored information to apparatus 10 for processing and display.

Apparatus 10 can also include an injector mechanism 32 which serves for injecting a cytotoxic agent into tissue to be treated. Injector mechanism 32 can include a reservoir 34 for storing the cytotoxin being in fluid communication with an injector port 36 which serves for delivering the cytotoxin to the tissue. Preferably, injector port 36 forms a part of electrodes 14 and/or 16 (e.g., hollow electrodes).

Apparatus 10 can further include a lighting source which serves for lighting the treated area allowing an operator of apparatus 10 to accurately place electrode system 12.

Apparatus 10 can be used in conjunction with imaging systems such as X-ray and ultrasound which can serve for directing electrodes 14 and 16 from outside the body into the target tissue.

Thus, the present invention provides methods and an apparatus which can be used to treat tumor tissue easily, safely and effectively. As clearly illustrated by the results presented hereinunder, the method of the present invention is clearly superior to all know prior art methods in that it can be used to directly destroy primary tumors and facilitates the destruction of residual metastatic disease by eliciting an anti tumoral immune/inflammatory response.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention are well known to the skilled artisan. Other general references are provided throughout this document. The procedures therein are believed to be well known in the art and are provided for the convenience of the reader. All the information contained therein is incorporated herein by reference.

Example 1

Life Expectancy Prolongation and Cure of Mice Bearing CT-26 Colon Carcinoma by Low-strength Electric Field Enhanced Cancer Chemotherapy Colorectal carcinoma is the second most frequent malignancy in Western world—it is estimated that there are nearly 400,000 deaths from CRC worldwide annually. Surgery can cure approximately 50% of patients and the overall five-year survival of patients with CRC is on the order of 50-55%. However, a considerable number of patients cannot undergo surgery, even at an early stage of the disease, due to severe complications. Therefore, effective treatment modalities for patients who cannot undergo surgery or have recurrent disease are highly desirable. Low electric field enhanced cancer chemotherapy (LEFCT-EC) represents a potentially valuable treatment option in such patients. Thus, in order to determine the potential of LEFCT-EC to enhance treatment of colon carcinoma, mice bearing tumors of a metastatic colon carcinoma cell line were treated with LEF in conjunction with different chemotherapeutic drugs, and the effect of the treatment on primary tumor growth, survival time and cure rate was analyzed as follows.

Materials and Methods:

Mice: BALB/C male mice were obtained from the breeding colony of Tel-Aviv University, Israel. Mice were used at 8-12 weeks of age. Animal care and experimentation were performed in accordance with the Tel-Aviv University guidelines.

Tumor: Colon carcinoma tumors were grown in mice with CT-26, a metastatic colon carcinoma cell line induced in a BALB/c mouse by chemical carcinogenesis. Cells were cultured in Dulbecco's modified Eagle's medium (DMEM) supplemented with 100 U/ml penicillin, 100 µg/ml streptomycin, 2 mM L-glutamine; 1 mM sodium pyruvate; 1% nonessential amino acid solution; 10% heat-inactivated fetal calf serum. Cultures were maintained at 37° C. in a humidified incubator with a 5% $CO_2$ atmosphere.

Tumor cell inoculation: Mice were inoculated intracutaneously with $10^5$ CT-26 cells suspended in 100 µL PBS into the low lateral side of the back. Local tumor growth was determined by measuring three mutually orthogonal tumor diameters with a caliper. The volume of tumor was calculated using the formula: $Vol = D1 \times D2 \times D3 \times \pi/6$, where D1, D2, D3 are three mutually orthogonal tumor diameters.

Electric field monitoring: Electric fields were monitored using an electric pulse generator CRASS S48 stimulator (CRASS medical instruments, Quincy, Mass., USA), and a COS 5020-ST digital oscilloscope (20 MHz).

Low-strength electric field stimulation: To subject tumors to LEFs, stainless steel needles were used as electrodes. Tumors 5 mm in diameter (about 65 $mm^3$) were transfixed by electrode needles, with one cathode in the center of the tumor and three or four peripheral anodes. The electrodes were connected to an electric pulse generator and to an oscilloscope. Pulsed LEFs with a repetition frequency of 500 Hz and a pulse width of 180 µs were applied at 20, 40, 60 and 70 V/cm for a duration 12 min or 20 min. The electric pulses were administered 2-4 min following chemotherapeutic drug administration. Mice were anesthetized 10 min before the procedure.

Chemotherapeutic agents: Bleomycin (Sigma Israel Chemicals Ltd., Israel; Megapharm Ltd., Israel) was kept at a temperature of 2-8° C., and was dissolved in pyrogen-free PBS to a concentration enabling dosages of 50 U/kg body weight prior to use. BCNU was administered at a dosage of 35 mg/kg body weight, and 5-FU (Abic, Israel) was used at a dose of 100 mg/kg body weight.

Anesthesia: Mice were anesthetized using an anesthetic cocktail comprising a dose of imalgen at 100 mg/kg body weight and xylazine hydrochloride at 6.25 mg/kg body weight dissolved in PBS injected intraperitoneally in a volume of 0.25 ml per mouse 10 min prior to LEF treatment.

Statistical analysis: Survival times (Kaplan-Meir test), survival comparisons between groups (Mantel-Cox test), and tumor volume differences between groups were plotted using StatSoft "Statistica" statistical software.

Experimental Results:

Cure of mice bearing metastatic colon carcinoma tumors via LEF treatment alone: In order to examine the influence of LEF alone on development of CT-26 tumors, mice were inoculated subcutaneously or intracutaneously with $10^5$ CT-26 tumor cells. When tumors reached a mean diameter of 5 mm, LEF treatments were applied and survival and tumor volume were monitored. The energy between two electrodes under different electric pulses was also calculated.

As is demonstrated in FIGS. 1a-b, treatment with LEF alone was unexpectedly found to be capable of enhancing survival. Whereas one half of untreated mice remained alive after about 42 days, one half of mice treated with a LEF of 20

V/cm remained alive after 62 days, one half of mice treated with a LEF of 40 V/cm remained alive after 68 days, and 70% of mice treated with LEFs of 60 or 70 V/cm remained alive after 90 days, the final time point of the experiment. Thus, treatment of tumor bearing mice with LEFs of 60 and 70 V/cm resulted in a 70% cure rate. Statistical analysis of these results is shown in FIG. 1b.

Figure 2:
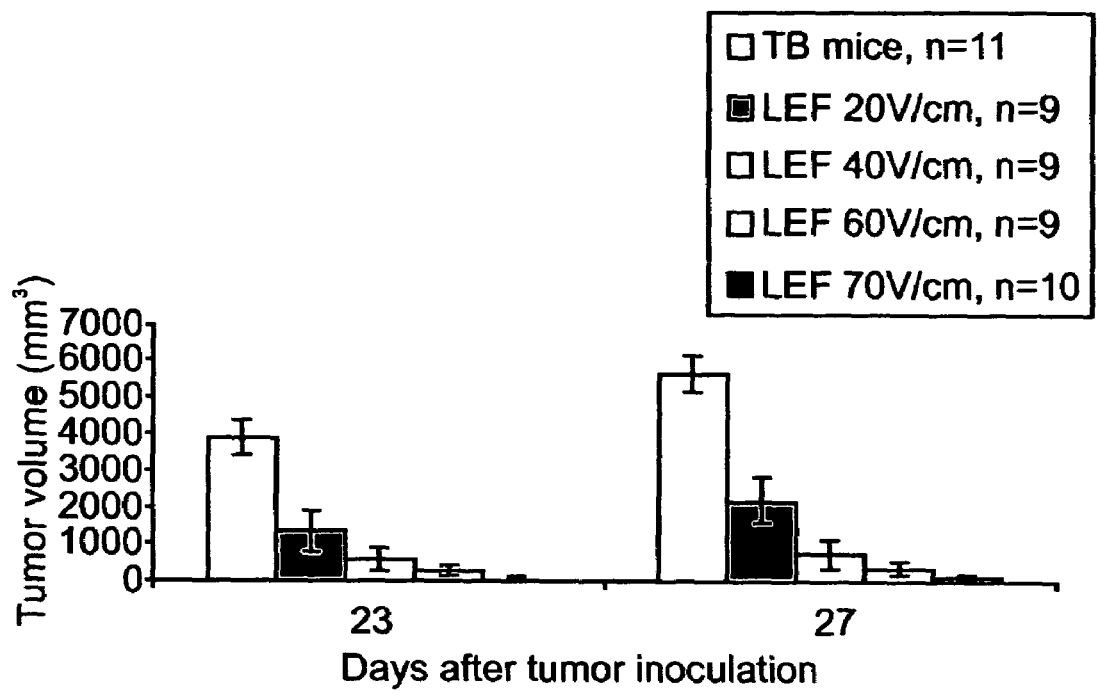
FIG. 2 is a histogram depicting the effect of LEF treatment alone on tumor size in CT-26 tumor bearing mice. Untreated tumor bearing mice (TB).

As is shown in FIG. 2, treatment with LEF alone was similarly unexpectedly found to be capable of greatly reducing tumor size, proportionally to the strength of the field applied. Whereas the tumor volumes of untreated mice had reached more than 5,500 mm$^3$ after 27 days, mice treated with a LEF of 70 V/cm did not display detectable tumors.

Figure 3:
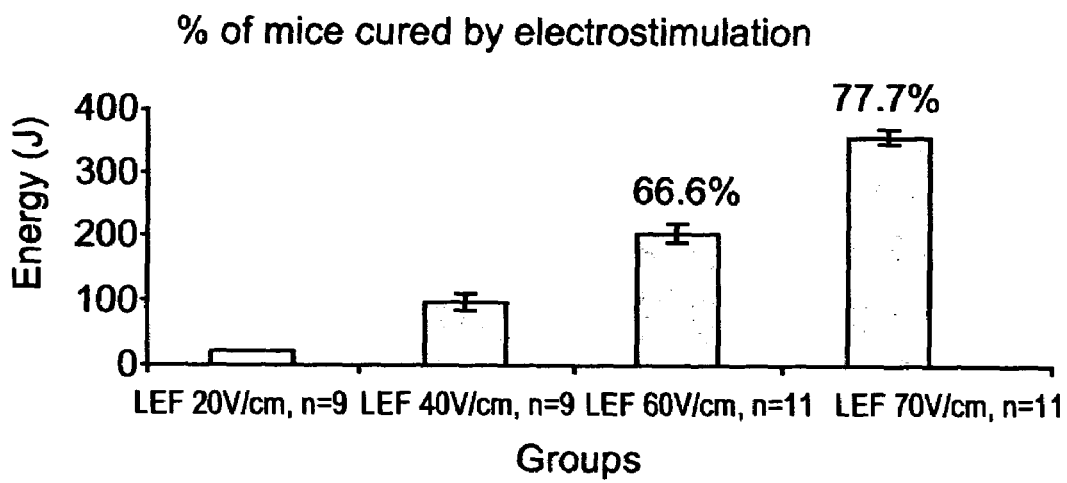
FIG. 3 is a histogram depicting the energy (in Joules) measured between electrodes when applying LEFs.

FIG. 3 shows the energy measured between electrodes when applying LEFs.

Figure 4A:
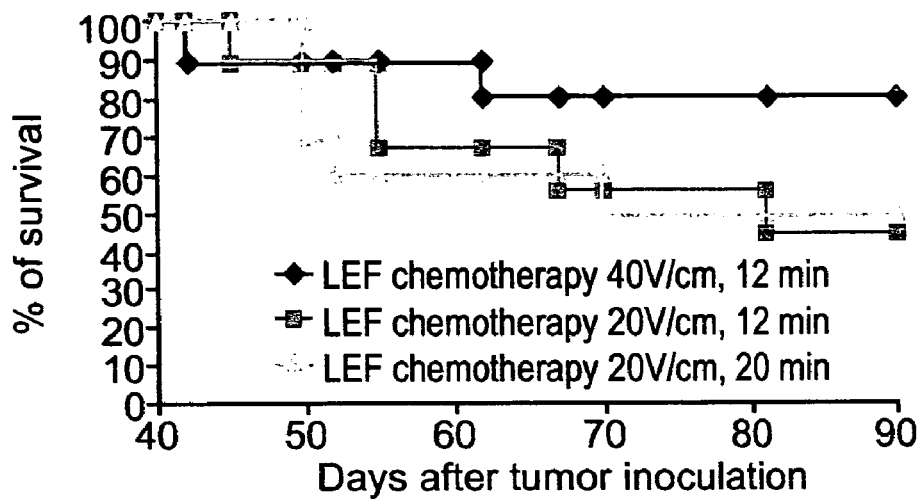
Figure 4B:
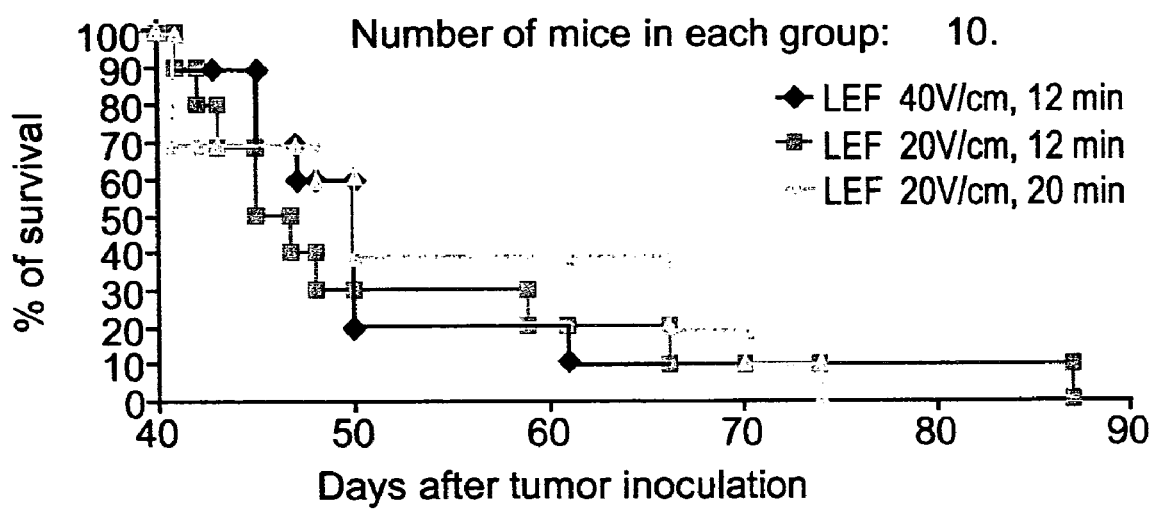

Effect of LEF duration and strength on potentiation of bleomycin for treatment of colon carcinoma: In order to determine the optimal LEFCT-EC/bleomycin therapy for treatment of colon cancer, mice bearing CT-26 tumors were treated with LEFs of 40 V/cm for 12 min, and 20 V/cm for 12 or 20 min with or without administration of bleomycin, and survival was analyzed. As is shown in FIGS. 4a-c, the optimal LEFCT-EC/bleomycin treatment was found to be administration of bleomycin in conjunction with treatment with LEF of 40V/cm for 12 min. In all combinations tested, survival was greatly enhanced when administering bleomycin in conjunction with LEF treatment than LEF treatment alone (FIGS. 4a and 4b, respectively). Statistical analysis of results obtained in FIGS. 4a and 4b are shown in FIG. 4c.

LEF treatment enhances anti-colon cancer activity of BCNU, bleomycin or 5-FU: In order to determine the efficacy of using LEFCT-EC with the chemotherapeutic drugs BCNU, bleomycin or 5-FU for treatment of colon carcinoma, mice bearing CT-26 tumor cells were treated with these drugs in conjunction with application of LEF (40 V/cm, for 12 min) and survival and/or tumor size was monitored.

Figure 5A:
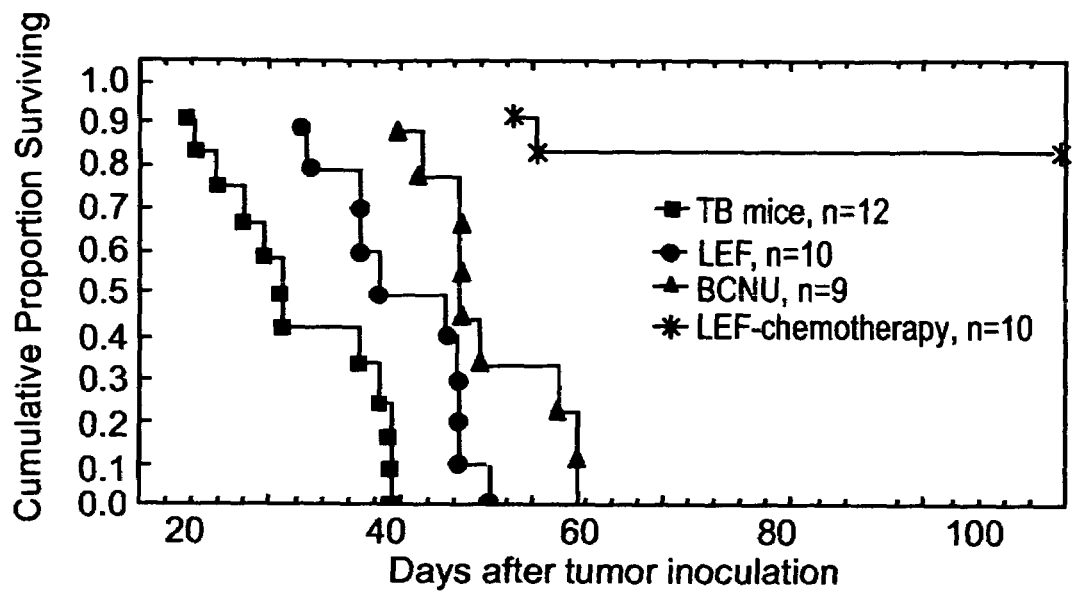
FIGS. 5a-b are a data plot depicting survival and a histogram depicting tumor size, respectively, in CT-26 tumor bearing mice treated with LEF, BCNU or both. TB—untreated tumor bearing mice. BCNU was injected intratumorally at a dose of 35 mg/kg body weight. Cumulative survival data were compiled from two separate experiments and statistical analysis was assessed by the Mantel-Cox test.
Figure 5B:
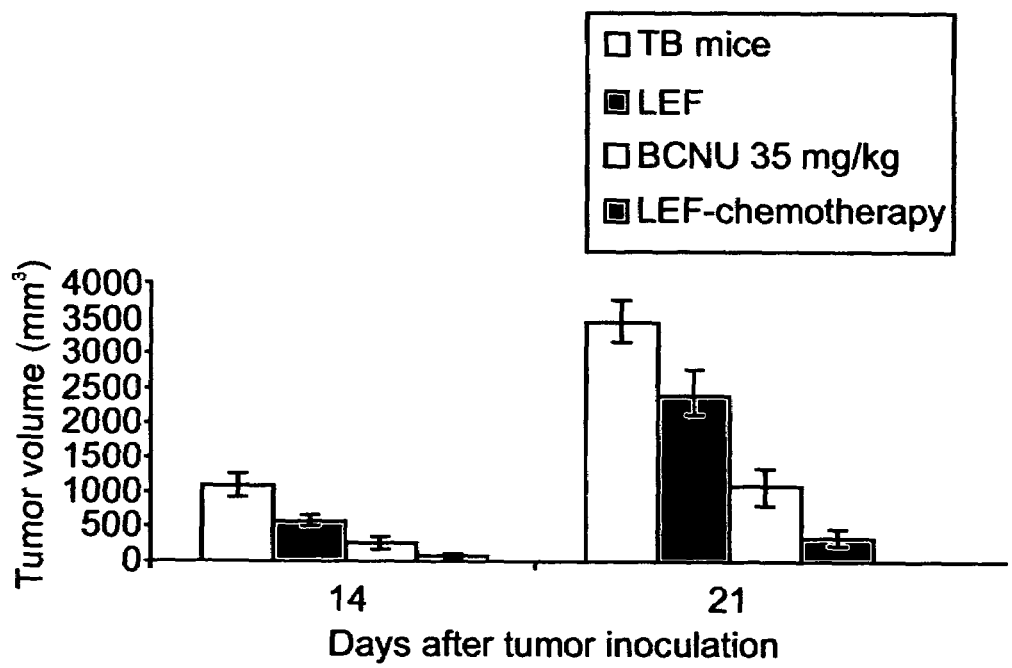

As is illustrated in FIG. 5a, whereas half the mice treated with intratumoral injection of BCNU alone died after about 48 days, the use of this drug in conjunction with LEF treatment led to a very high increase in the survival rate, as demonstrated by a survival rate of 83% after 52 days which remained unchanged until day 110, the final time point of the experiment. FIG. 5b similarly demonstrates a very strong potentiation of BCNU induced tumor size reduction by LEF treatment since, after 21 days, tumors in mice treated with the drug only were about triple the size of those in mice treated with both BCNU and LEF. Thus, LEFCT-EC treatment of tumor bearing mice with BCNU resulted in an 83% cure rate.

Figure 6A:
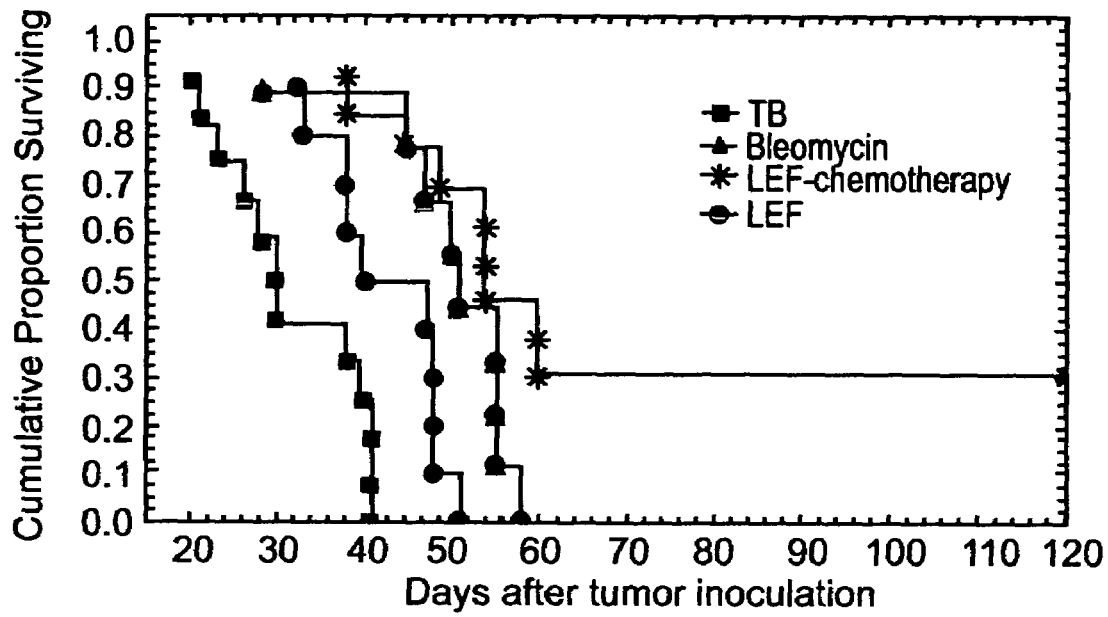
FIGS. 6a-b are a data plot depicting survival and a histogram depicting tumor size, respectively, in CT-26 tumor bearing mice treated with LEF, bleomycin or both. TB—untreated tumor bearing mice. Cumulative survival data were compiled from two separate experiments. Number of mice in each group: 9-13. Statistical analysis was assessed by the Mantel-Cox test.
Figure 6B:
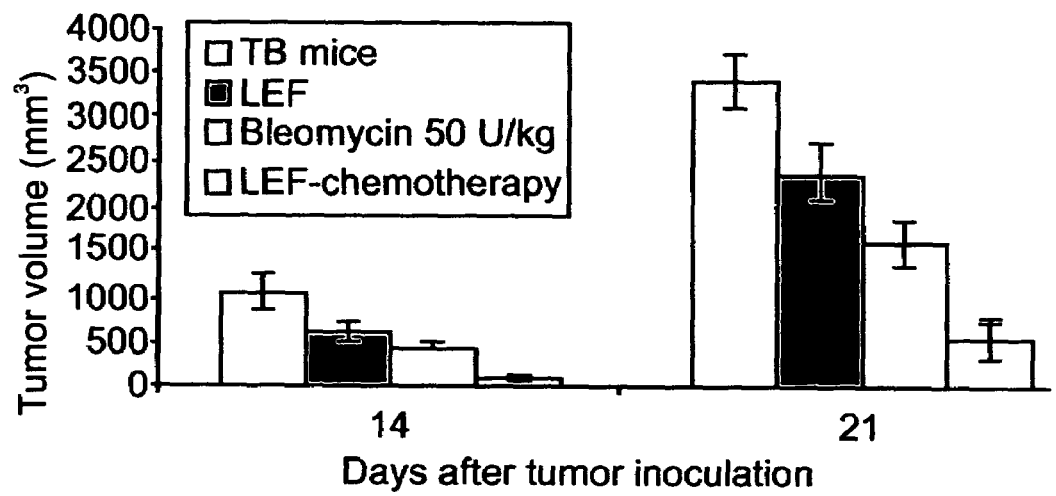

As shown in FIG. 6a, whereas half the mice treated with intratumoral injection of bleomycin alone died after about 51 days, the use of this drug in conjunction with LEF treatment led to a significant enhancement in the survival rate, as demonstrated by a survival rate of 33% after 60 days which remained unchanged until day 120, the final time point of the experiment. Likewise, FIG. 6b shows a very strong potentiation of bleomycin induced tumor size reduction by LEF treatment since after 21 days—tumors in mice treated with the combination of the drug and LEF were less than half the size of those in mice treated with the drug only. Thus, LEFCT-EC treatment of tumor bearing mice with bleomycin resulted in a 33% cure rate. Statistical comparison of the kinetics of survival in untreated mice with the LEF-chemotherapy group yielded P=0.00001.

Figure 7:
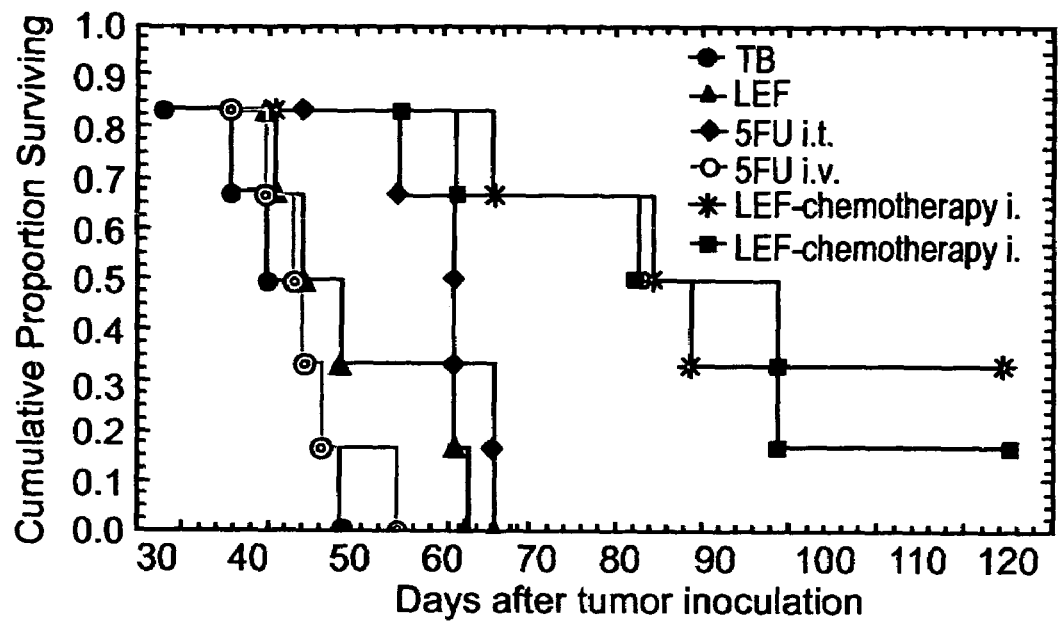
FIG. 7 is a data plot depicting survival of CT-26 tumor bearing mice treated with LEF, 5-FU, or both. TB—untreated tumor bearing mice. Mice were treated with 100 mg/kg 5-FU either intravenously (i.v) or intratumorally (i.t). Statistical analysis was assessed by the Mantel-Cox test. Data was obtained from six mice per group.

As is illustrated in FIG. 7, half the mice treated with intratumoral or intravenous injection of 5-FU alone died between days 40 and 45, whereas mice treated with this drug in conjunction with LEF displayed a large increase in survival rate, since half of the mice treated with intratumoral or intravenous injection of 5-FU in conjunction with LEF treatment were still alive after 80 days. Statistical comparison of the survival kinetics of the untreated croup with the LEF-chemotherapy i.v. treated group yielded P 0.00051, and comparison of survival of the LEF-chemotherapy i.t. group with untreated mice yielded P=0.0049.

Figure 8:
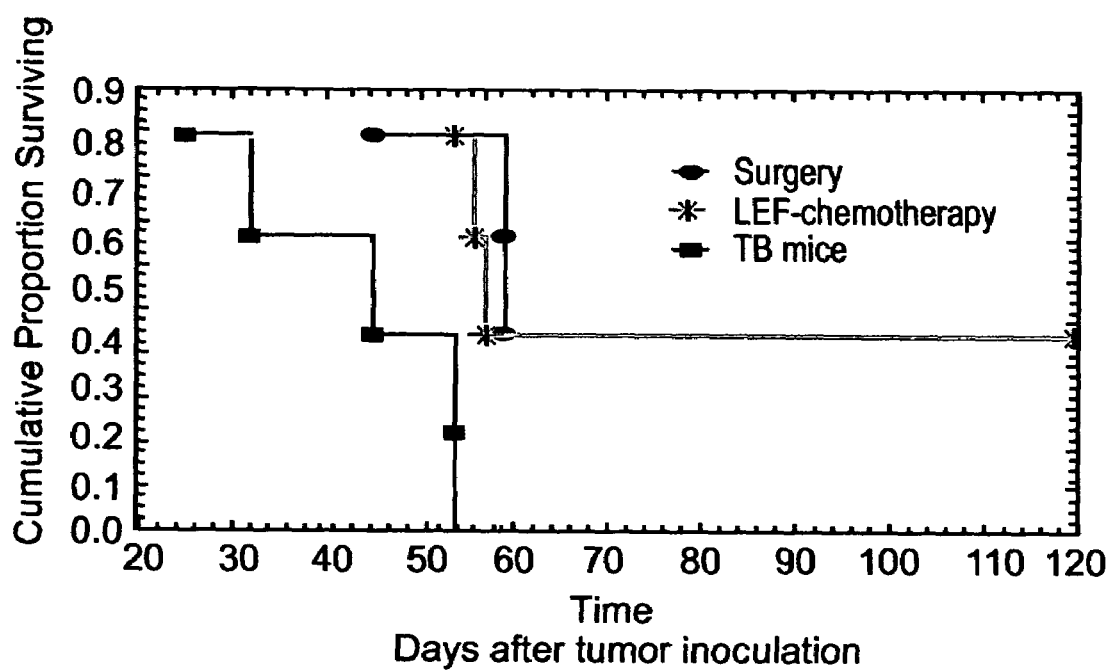
FIG. 8 is a data plot depicting survival of CT-26 tumor bearing mice treated with surgery or BCNU in conjunction with LEF treatment. TB—untreated tumor bearing mice. Statistical analysis was assessed by the Mantel-Cox test. Data was obtained from 5 mice per group.

LEFCT-EC with BCNU is as efficient as surgery for treatment of metastatic colon carcinoma in mice: In order to compare the potential efficacy of LEFCT-EC with that of surgery for treatment of colon carcinoma, mice bearing CT-26 tumors 5 mm in diameter had tumors removed surgically or were treated with a combination of LEF of 40 V/cm and BCNU. As can be seen in FIG. 8, whereas all untreated mice had died after 54 days, mice treated with surgery or LEF in conjunction with BCNU displayed similarly enhanced 40% survival after about 60 days until after about 120 days, the final time point of the experiment. Statistical comparison of survival kinetics of untreated mice with the surgically treated group yielded P=0.018.

Involvement of immune and/or inflammatory mechanisms in the cure of CT-26 tumor bearing mice treated via LEFCT-EC with BCNU:

Mice cured of metastatic colon carcinoma by LEFCT-EC with BCNU develop resistance to subsequent tumor: In order to examine whether mice cured of CT-26 tumors via LEFCT-EC with BCNU become resistant to growth of such tumors, cured mice were challenged 80-120 days following the first inoculation with the same dose of $10^5$ CT-26 cells as the first inoculation, and the animals were monitored for tumor growth and survival.

Figure 9A:
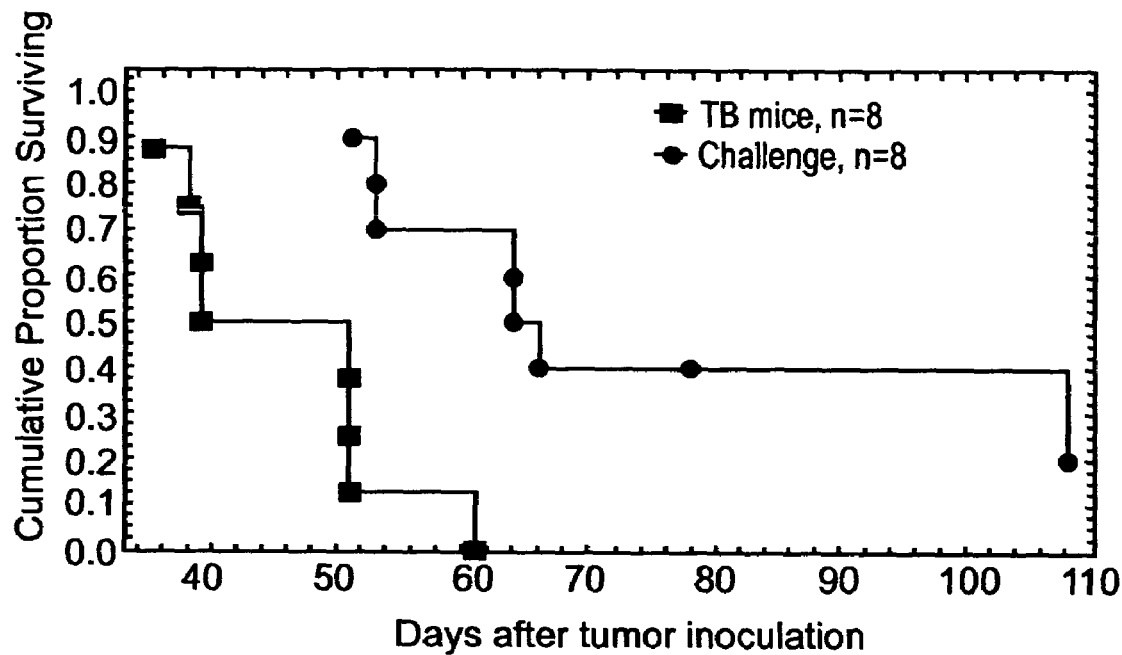
FIGS. 9a-b are a data plot depicting survival and a histogram depicting tumor size, respectively, in mice cured of CT-26 tumors via low electric field enhanced cancer chemotherapy (LEFCT-EC) with BCNU and subsequently rechallenged with the same initial lethal dose of CT-26 cells. TB mice—mice inoculated for the first time with $10^5$ CT-26 cells. Challenge—mice cured by LEFCT-CT and challenged with $10^3$ CT-26 cells.
Figure 9B:
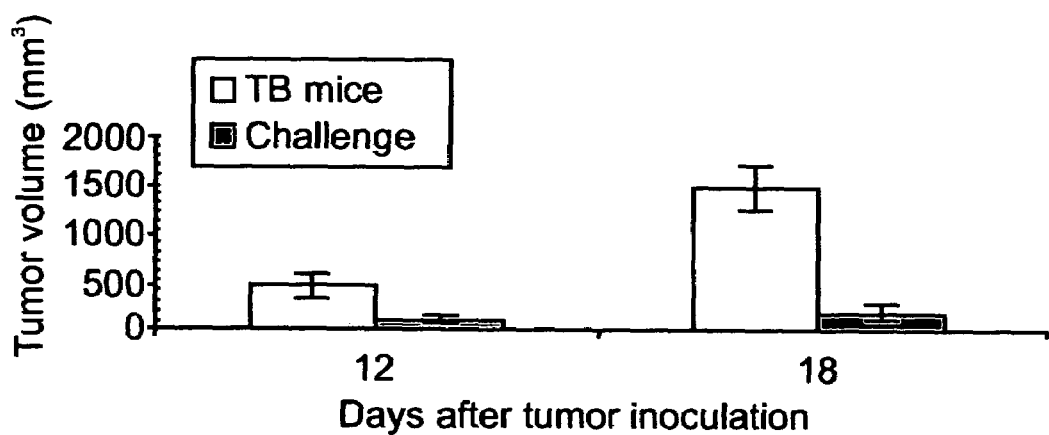

As is illustrated in FIG. 9a, whereas only half of the mice inoculated for the first time with CT-26 cells remained alive by about day 37, half of the cured and challenged mice were still alive by about day 63. Similarly, the results shown in FIG. 9b show that after 18 days the volumes of the tumors of the reinoculated mice were about one order of magnitude smaller than those of mice inoculated for the first time. Thus, cure of CT-26 tumors via LEFCT-EC clearly has the capacity to induce a protective effect against subsequent challenge with this tumor. Statistical comparison of the survival kinetics of tumor bearing mouse group with the challenged group yielded P=0.00002.

Figure 10A:
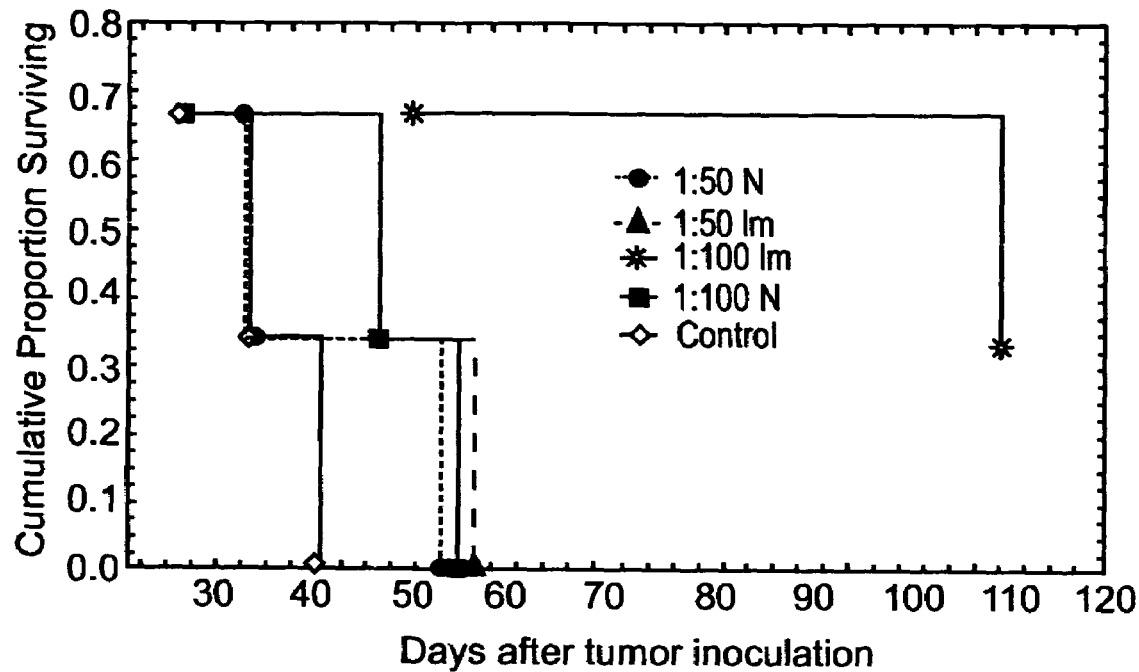
FIGS. 10a-b are a data plot depicting survival and a histogram depicting tumor size, respectively, in mice inoculated with CT-26 cells mixed with splenocytes of mice cured of CT-26 tumors via LEFCT-EC. Mice were inoculated with $10^5$ CT-26 cells only (control; TB mice), or with 105 CT-26 cells mixed with either splenocytes of normal (N; norm) or cured (Im; immune) mice in a ratio of CT-26 cells to splenocytes of 1:50 or 1:100.
Figure 10B:
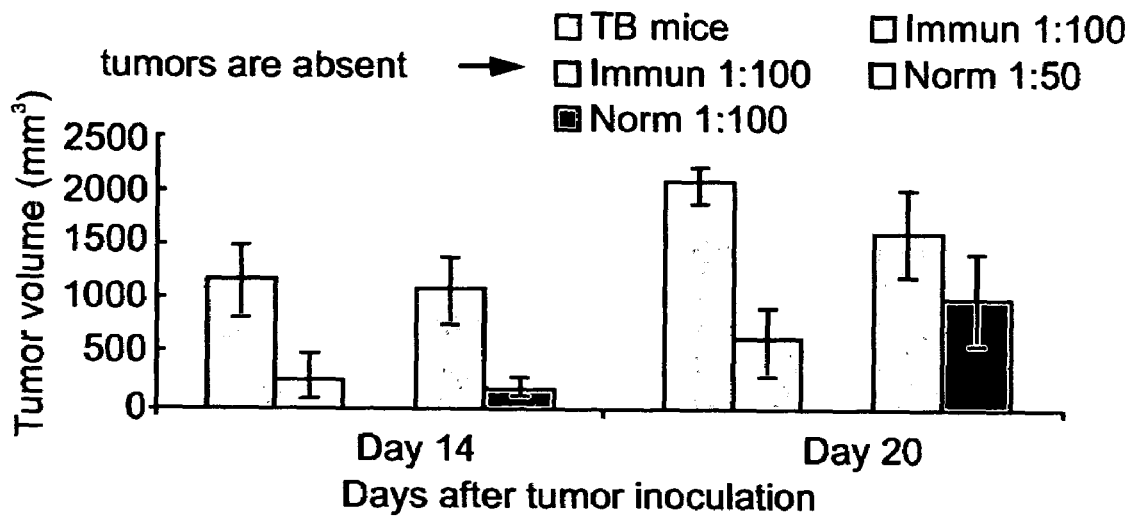

Anti-tumor effect of splenocytes from tumor bearing mice cured by LEFCT-EC with BCNU: In order to examine whether development of resistance against challenge with CT-26 tumors in mice cured of such tumors via LEFCT-EC with BCNU is immunologically mediated, normal mice were inoculated with a dose of CT-26 tumor cells mixed with splenocytes from cured animals. The results presented in FIGS. 10a-b clearly indicate that splenocytes from cured mice have the capacity to greatly enhance the survival (FIG. 10a) and to completely prevent growth of tumors (FIG. 10b) in mice inoculated with CT-26 cell splenocytes from cured mice inoculated with CT-26 cells and splenocytes at a ratio of tumor cells to splenocytes of 1:100. Thus, curative LEFCT-EC+BCNU treatment of CT-26 tumor bearing mice induces immunological resistance to subsequent growth of such tumors in such mice.

Effect of LEFCT-EC with BCNU on CT-26 development in mice bearing large tumors: In order to examine the effectiveness of LEFCT-EC with BCNU on tumor development in mice with a large tumor burden, mice bearing tumors of 10 mm (about 523 mm$^3$) or 15 mm in diameter (about 1,760 mm$^3$). These animals were treated with 4 electrodes placed 7 mm apart.

As is demonstrated in FIGS. 11a-c, treatment of mice via LEFCT-EC with BCNU was capable of curing a very high percentage of animals. Whereas treatment with BCNU only led to death of all mice after 90 days, treatment with LEFCT-EC alone led to 30% survival after 120 days, and treatment via LEFCT-EC with BCNU led to a cure rate of over 80% of the mice (FIG. 11a). Similarly, as is shown in FIG. 11b, the size of tumors in mice treated via LEFCT-EC with BCNU was approximately an order of magnitude smaller than that in mice treated via BCNU alone. Statistical analysis of the results obtained in FIG. 11a are shown in FIG. 11c.

As is demonstrated in FIGS. 12a-c treatment of tumor bearing mice via LEFCT-EC with BCNU led to a 100% cure rate and complete prevention of tumor growth. Whereas treatment with BCNU only or surgery only led to death of all mice after 87 and 84 days, respectively, treatment of mice with LEF only or LEF with BCNU led to about 20% and, most dramatically, to 100% survival after 100 days, respectively (FIG. 12a). Similarly, as is shown in FIG. 12b, no tumors were detected after 42 days in mice treated via LEFCT-EC with BCNU, unlike in mice which were treated with only, BCNU LEF or surgery. Statistical analysis of the results obtained in FIG. 12a are shown in FIG. 12c.

These results therefore demonstrate the startling discovery that LEF treatment alone has the capacity to lead to a high cure rate of animals bearing metastatic colon carcinoma tumors and that treatment via LEFCT-EC with BCNU can be 100% curative in mice bearing CT-26 colon carcinoma tumors, and that LEF treatment also enhances the anti colon cancer activity of bleomycin and 5-FU. Furthermore, these results also show that LEFCT-EC with BCNIJ is as efficient as surgery for treatment of small metastatic colon carcinoma in tumor bearing animals, that animals cured of metastatic colon carcinoma by LEFCT-EC with BCNU develop resistance to subsequent tumor growth, and that LEFCT-EC with BCNU represents a treatment modality which is more potent than surgery against large colon carcinoma tumors. Thus, the method of the present invention represents a potent and novel means of treating colon cancer being clearly superior to all prior art methods.

Example 2

Tumor Growth Retardation and Cure of B16 Melanoma Bearing Mice by Low-strength Electric Field Enhanced Cancer Chemotherapy Melanoma is a very aggressive type of skin cancer whose incidence is on the increase and which has a very high mortality rate. There do not exist any satisfactory treatment modalities for this dangerous disease. Since it has previously been demonstrated that treatment of cells with LEFs has the capacity to lead to efficient cellular uptake of macromolecules, the capacity of LEF treatment to enhance uptake of chemotherapeutic agents by melanoma cells, thereby potentiating their anti melanoma activity, was demonstrated as follows.

Materials and Methods:

Animals: C57BL/6 male mice were obtained from the breeding colony of Tel-Aviv University, Israel. Mice were used at 8-12 weeks of age. Animal care and experimentation was carried out in accordance with Tel-Aviv University guidelines.

Melanoma tumor cell line: The highly metastatic, poorly immunogenic B16-F10.9 (F10.9) subclone of the B16 melanoma cell line was used to generate melanoma tumors in mice (Eisenbach L. et al., 1984. Int J Cancer 34:567). Cells were maintained in DMEM supplemented with 100 U/ml penicillin, 100 µg/ml streptomycin, 4 mM glutamine, 1 mM sodium pyruvate, 1% non-essential amino acids and 10% heat-inactivated fetal calf serum (FCS); and were cultured at 37° C. in a humidified incubator in an atmosphere of 7% carbon dioxide and 93% air.

Tumor generation protocol: F10.9 tumors were induced in C57BL/6 mice by subcutaneous injection of $2\times10^5$ F10.9 cells. Mice were subjected to experimental treatments once tumors reached 5 mm in diameter (about 60-70 $mm^3$). Chemotherapeutic drugs: The following chemotherapeutic drugs used were: cis-platinum (II) diamminedichloride (cisplatin; #P-4394, Sigma, Israel), dissolved in PBS for injections; Taxol (Mead Johnson Oncology Products, A Bristol-Myers Squibb, USA), obtained as a sterile nonpyrogenic solution containing 6 mg/ml paclitaxel, 527 mg/ml of purified Cremophor EL (polyoxyethylated castor oil) and 5-FU (Abic, Israel).

Reagents: Reagents used include oleum ricini (Floris, Israel), eosin alcoholic with methanol (Pioneer Research Chemicals, UK), Harris's haematoxylin (Pioneer Research Chemicals, UK) and buffer formaldehyde (Frutarom, Israel).

Antibodies: Antibodies used for immunohistochemistry were rat anti mouse CD3 (#MCA1477, Serotec, USA), rat anti mouse F4/80 antigen (#MCA497, Serotec, USA), and the monoclonal antibody F7-26 (#804-192-L001, Alexis, USA).

Low-strength electric field enhanced cancer therapy protocol: Mice were subjected to a single treatment of LEFCT-EC, once tumors reached 5 mm in diameter (11-17 days following tumor cell inoculation). Volumes of up to 100 µl of chemotherapeutic agents were injected into tumor loci, and exposures to electric fields were carried out 3-4 min following intratumoral injection of chemotherapeutic agents. To expose tumors to electric fields, stainless steel electrode needles (Karlsbader insect pins No 0. BioQuip Products, USA) soldered at their brassy ends with thin isolated copper wires were used. Electrodes were inserted to a depth of about 7 mm percutaneously into and in the immediate vicinity of the tumor; one cathode needle in the center of the tumor and three peripheral anodes, at a distance of about 5 mm from the cathode. The needles were connected to an electric pulse generator (Grass S48 Stimulator, USA). The field strength applied was about 40 V/cm; the repetition frequency, 500 Hz; and the pulse width, 180 µs. All mice were anesthetized prior to LEF treatment.

Anesthesia: performed as described above in Example 1 of the Examples section.

Statistical analysis: Statistical analysis of survival times (Kaplan-Meir test), survival comparisons between groups (Mantel-Cox test) and tumor volume differences between groups (Kolmogorov-Smirnov test) were performed using StatSoft Statistica statistical software. The 10-15% mortality rate in the 5 days following LEF or LEF-chemotherapy was considered as treatment-caused, therefore such cases of mortality were excluded.

Tumor volume determination: performed as described above in Example 1 of the Examples section.

Experimental Results:

Effect of LEFCT-EC on the survival of B16-F10.9 bearing mice using the chemotherapeutic agents cisplatin, taxol, bleomycin and 5-FU:

In the first phase of this study LEF treatments were used in combination with the chemotherapeutic agents cisplatin, taxol, bleomycin and 5-FU. The duration of electric stimulation in LEFCT-EC required for optimal results was investigated. Cisplatin (4 mg/kg body weight) was injected intratumorally followed by electrostimulation for 12, 15 or 20 minutes. There were no significant differences between the groups subjected to the different exposure periods, yet the mortality rate within a few days following the treatment was higher in the groups that were exposed to electric fields for 15 or 20 minutes compared with the ones exposed for only 12 minutes. Thus, the 12 min exposure period was chosen for the subsequent experiments.

Figure 13:
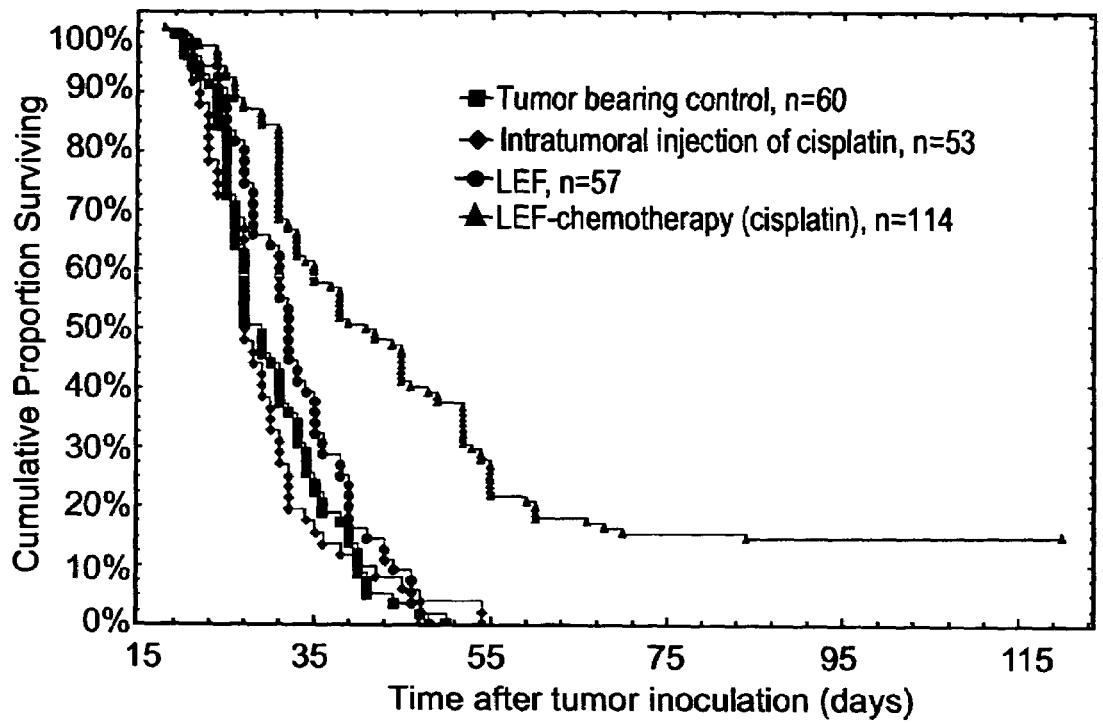
FIG. 13 is a data plot depicting cumulative survival of C57BL/6 mice bearing melanoma following LEFCT-EC with intratumoral cisplatin administration. Mice bearing 60-70 $mm^3$ subcutaneous tumors were subjected to LEF treatment alone or with cisplatin (4 mg/kg) injected intratumorally.

Anti-tumor effect of LEFCT-EC with cisplatin: The effect of treating F10.9 tumor bearing mice via LEFCT-EC with intratumoral cisplatin administration was analyzed. As is illustrated in FIG. 13, the mean survival time (MST) of LEF-chemotherapy treated mice (120 days after tumor inoculation) was 51.1 days, whereas non-treated tumor bearing animals had a mean survival of 30.3 days. Chemotherapy alone and electrostimulation alone yielded mean survival time of 29.5 and 32.8 days, respectively. Moreover, in the LEF-chemotherapy group 13.5% of the animals were tumor free 120 days after tumor inoculation. A Mantel-Cox statistical analysis showed a significant improvement (P<0.000004) in the survival of LEF-chemotherapy treated mice, compared with all other groups. Cisplatin or LEF alone had no significant effect. Thus, LEFCT-EC has the capacity to significantly potentiate the anti-melanoma effect of cisplatin.

Figure 14:
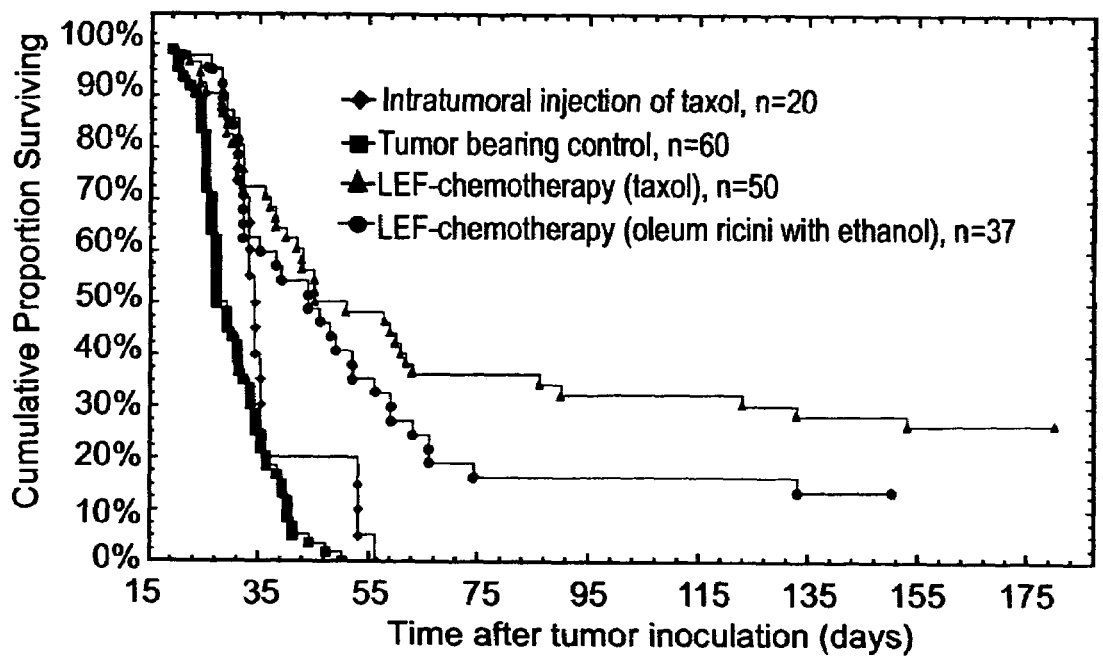
FIG. 14 is a data plot depicting cumulative survival of C57BL/6 mice bearing melanoma following LEFCT-EC with taxol. Mice bearing melanoma were treated either with taxol (20 mg/kg) alone, taxol in combination with LEF or by intratumoral injection of a mixture of oleum-ricini/ethanol (1:1 v/v) with LEF.

Anti tumor effect of LEFCT-EC with taxol: Similar experiments were performed with paclitaxel as a chemotherapeutic agent (20 mg/kg intratumorally). Since paclitaxel was dissolved in castor oil and ethanol, mice in the low-strength electric field stimulation control group were injected intratumorally with 100 µl of a mixture consisting of oleum ricini+ethanol (1:1 v/v) prior to the electro-stimulation. This mixture was selected to imitate the commercial solvent of paclitaxel, which consists of Cremophor EL (polyoxyethylated castor oil) and dehydrated ethanol in a 1:1 ratio. The results presented in FIG. 14 show that chemotherapy alone had no effect on the survival rate. The cure rate in the LEF-chemotherapy with taxol group reached 26% 180 days following tumor inoculation (P=0.00021, LEF-chemotherapy versus taxol). The mean survival of LEF-chemotherapy treated mice (180 days after tumor inoculation) was 83.5 days, chemotherapy alone—36.7 days and mixture of oleum ricini plus ethanol with LEF (150 days after tumor inoculation)—59.1 days. In addition, a 13.5% cure rate was obtained 150 days after tumor inoculation in mice, treated by the mixture of castor-oil/ethanol and LEF (LEF-chemotherapy vs. LEF, P=0.15841).

Anti tumor effect of LEFCT-EC With bleomycin: A dose of 8 U/kg body weight of bleomycin was used for these experiments. The survival of mice, treated with the different protocols is shown in FIG. 15. Untreated mice had a mean survival time of 30.2 days and those treated with LEF alone had a MST of 30.9 days. Mice, treated with bleomycin alone had a MST of 34.3 days, while LEF-chemotherapy treatment resulted in a notable prolongation of the MST to 48 days (180 days after tumor inoculation). Furthermore, in the LEF-chemotherapy group 8.2% of the animals were alive and free of visible tumor 180 days after tumor inoculation. Mantel-Cox analysis revealed a statistically significant difference between survival of mice in the LEF-chemotherapy group compared to control (P=0.00001) and LEF (P=0.002) groups, but not compared to the one treated with chemotherapy alone (p=0.074).

Figure 16:
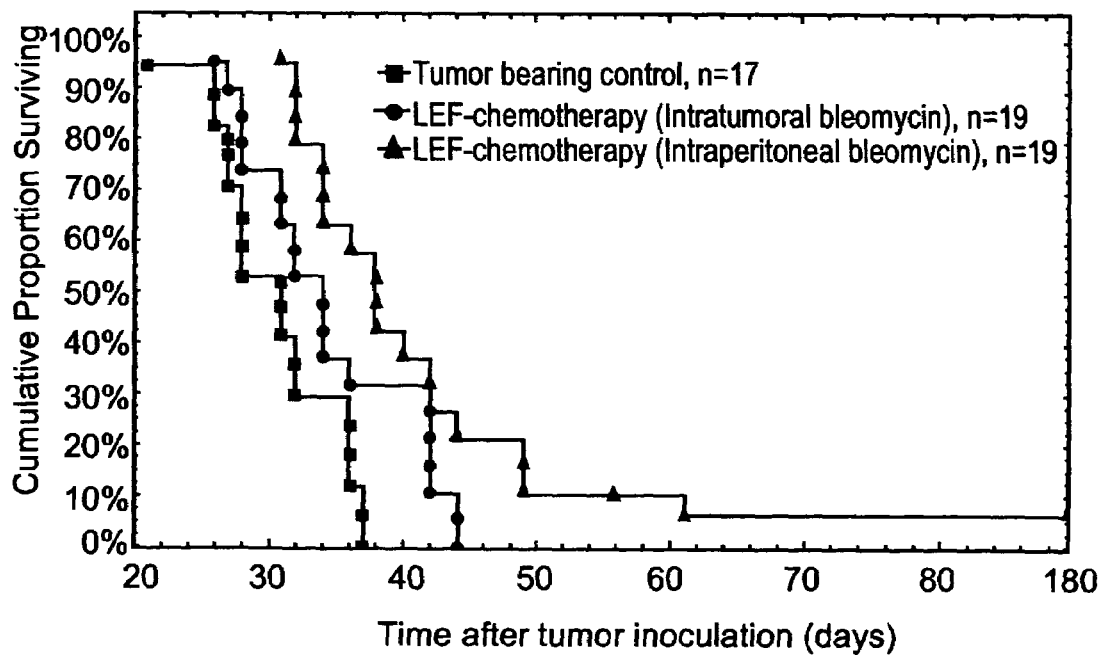
FIG. 16 is a data plot depicting the effect of LEF with either intratumoral or intraperitoneal administration of bleomycin on cumulative survival of C57BL/6 mice bearing melanoma.

The significance of the mode of drug injection on the efficacy of LEFCT-EC with bleomycin was also tested. Mice with 5 mm diameter tumors were treated by LEFCT-EC with bleomycin (8 U/kg) administered either intratumorally or intraperitoneally. The results presented in FIG. 16 reveal a longer MST of the LEF-chemotherapy group which received the chemotherapy intratumorally (46.6 days), as compared to the LEF-chemotherapy group injected intraperitoneally (34.6 days). Statistical analysis of survival rate showed a notable difference between the two groups (P=0.048). In addition, 5% of the animals from the LEF-chemotherapy group treated intratumorally were alive 180 days following tumor inoculation.

About 10% of LEFCT-EC treated mice either with cisplatin, taxol or bleomycin died two months and later after the treatment. Although these animals were completely free of primary tumor, with full skin recovery, autopsy revealed visible pulmonary metastatic foci.

Anti tumor effect of LEFCT-EC with 5-FU: Treatment of tumor bearing mice via LEFCT-EC with 5-FU (150 mg/kg) was found to be beneficial for inhibition of primary tumor growth (Table 1).

TABLE 1

Effect of LEFCT-EC with 5-FU treatment on tumor growth

| Treatment[a] | Size[b] (mean ± standard error, mm$^3$) | | | |
|---|---|---|---|---|
|  | cisplatin | bleomycin | 5-FU | taxol |
| LEF-CT | 83 ± 57 | 573 ± 138 | 143 ± 52 | 71 ± 25 |
| Intratumoral drug injection | 1684 ± 204 | 2456 ± 220 | 460 ± 54 | 927 ± 177 |
| LEF | 914 ± 323 | 1792 ± 250 | 588 ± 143 | 126 ± 34[c] |
| Untreated tumor-bearing animal | 4972 ± 358 | 5823 ± 604 | 4802 ± 549 | 5078 ± 535 |

[a]B16-F10.9 melanoma bearing mice were treated by LEFCT with cisplatin (4 mg/kg), bleomycin (8 U/kg), 5-FU (150 mg/kg) or taxol (20 mg/kg), by chemotherapy or electric stimulation alone, or no treated.
[b]Tumor size was measured 7 days after treatment.
[c]The mixture of oleum ricini with ethanol was injected intratumorally in this group.

Effect of LEFCT-EC on primary tumor size: Tumor volumes 7 days following cisplatin, taxol, bleomycin and 5-FU treatment is shown in Table 1. Tumor volume values were obtained as the average of at least 20 tumors. In all LEFCT-EC treatments, tumors were much smaller than in control groups (LEFCT-EC versus LEF, p<0.01 for cisplatin, 5-FU and bleomycin groups, and p<0.05 for taxol group). The most notable effect on primary tumors was achieved using LEFCT-EC with taxol.

Effect of curative LEFCT-EC treatment on generation of anti B16-F10.9 tumor resistance: The resistance of mice cured of B16-F10.9 melanoma by LEF-chemotherapy was analyzed by challenging such cured mice with a tumorigenic dose of B16-F 10.9 melanoma cells.

Figure 17:
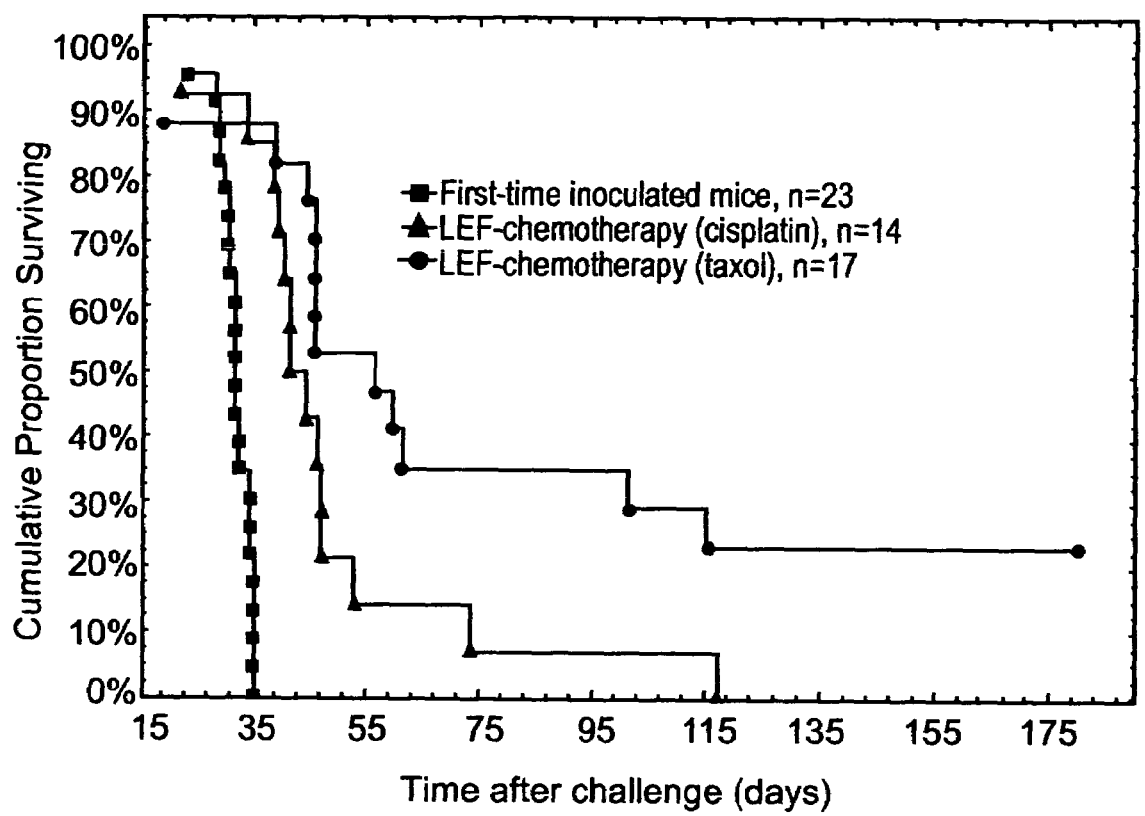
FIG. 17 is a data plot depicting the cumulative survival of mice previously bearing B16-F10.9 melanoma and cured by LEFCT-EC with cisplatin or taxol following challenge with B16-F10.9 melanoma cells. Mice cured by LEF-chemotherapy that survived for 120-180 days after initial tumor inoculation, were challenged with $2 \times 10^5$ B16-F10.9 cells subcutaneously.
Figure 18A:
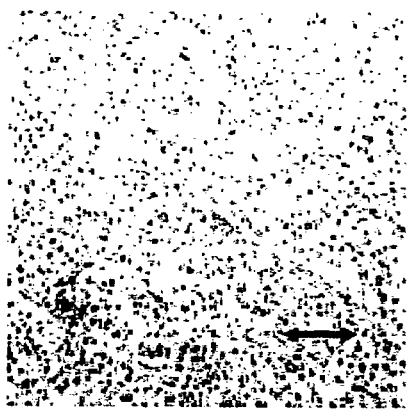
FIGS. 18*a-d* are photomicrographs depicting infiltration of lymphocytes (FIGS. 18*a-b*) and macrophages (FIGS. 18*c-d*) into tumor tissue 2 days following LEF-chemotherapy (FIGS. 18*b* and 18*d*).
Figure 18B:
Figure 18C:
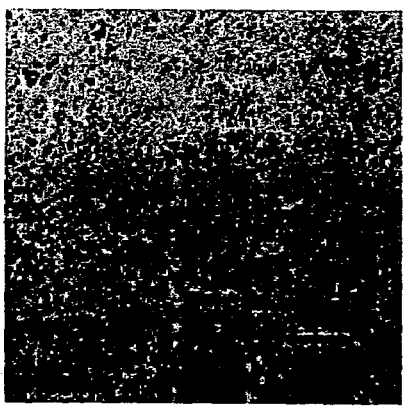
Figure 18D:
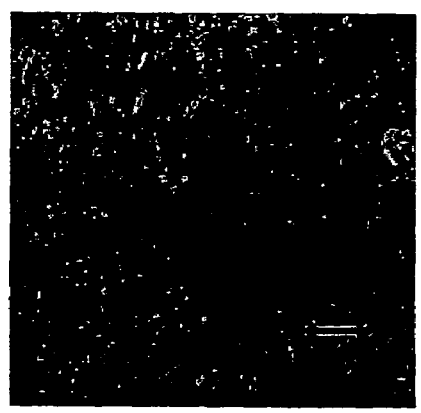

The results presented in FIG. 17 show that cured mice challenged with a tumorigenic dose of B16-F10.9 cells exhibited significantly prolonged survival compared to mice inoculated for the first-time. It can be also observed that mice cured by LEFCT-EC with taxol were rendered significantly more resistant to the challenge, as compared to the animals cured by LEFCT-EC with cisplatin (p=0.03481). The MSTs of first-time inoculated mice, and challenged mice previously cured by LEFCT-EC with cisplatin and by LEFCT-EC with taxol, were 31.3, 48.7 and 73.2 days, respectively. Moreover, about 23.5% (4 out of 17) of the challenged mice previously treated by LEFCT-EC with taxol did not develop tumor at all.

Histological examination of tumors: To ascertain the role of immune infiltration in primary tumor destruction following treatment with LEF alone or with taxol, tumors were ectomized at different times following treatment, and stained by haematoxylin and eosin, as well as reacted with anti-CD3, anti-F4/80 and F7-26 antibodies. Swollen cells with condensed nuclei were observed under the microscope 3-4 hours following LEF and LEF-chemotherapy. Most noticeable necrotic lesions with infiltrates were seen 48-72 hours following LEFCT-EC. Massive infiltration of T-lymphocytes and macrophages, as compared to the untreated tumors, was observed 48-72 hours following the treatment (FIG. 18). Three to four hours after LEF or LEF-chemotherapy infrequent apoptotic regions were detected by immunostaining with F7-26 antibody. Two-three days after LEFCT-EC or LEF alone apoptotic cells became rare or absent in some of the sections. In the untreated tumors apoptotic cells were not found (results not shown).

Comparison of surgery and LEFCT-EC: To compare the efficacy of LEFCT-EC to that of conventional surgery and chemotherapy treatments, C57BL/6 male mice (8-12 weeks old) were injected with $10^5$ B16-F10.9 cells subcutaneously. Once the tumors reached 5 mm in diameter (11-17 days following inoculation), they were surgically removed. One experimental group received a single dose of taxol (20 mg/kg) subcutaneously in close proximity to the site of the operation one day following tumorectomy.

Figure 19:
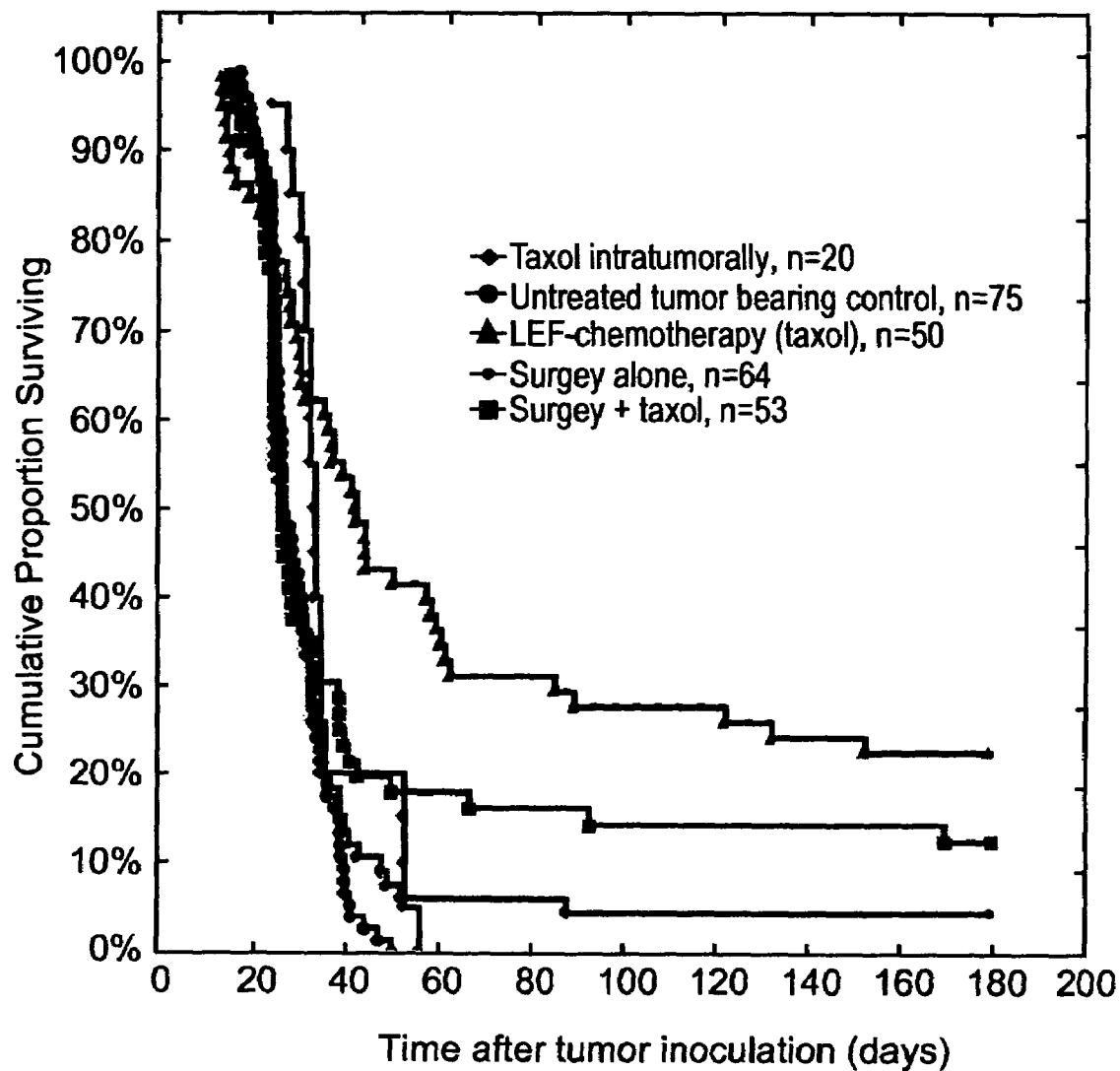
FIG. 19 is a data plot depicting the cumulative survival of C57BL/6 mice bearing subcutaneous B16-F10.9 melanoma following surgery with taxol or following LEF with taxol. In one treatment group, subcutaneous melanomas were surgically removed from tumor bearing mice, and part of the mice received 20 mg/kg taxol subcutaneously near the site of excision. In another treatment group, tumor bearing mice were treated via LEF with taxol.

The results of the experiment are shown in FIG. 19. Whereas less than 5% of the mice were cured by surgery alone, the use of taxol in addition to surgery increased the cure rate to 13%. The MST following surgery and surgery plus taxol treatments was 37 and 55 days, respectively. However, LEF-chemotherapy treatment resulted in a better effect in all checked parameters: a 26% cure rate and survival extension of 84 days (LEF-chemotherapy versus surgery+taxol, P=0.00131).

Conclusion: These results therefore demonstrate that LEFCT-EC significantly potentiates the anti melanoma activity of cisplatin, taxol, bleomycin and 5-FU, and that animals cured of melanomas using LEFCT-EC are endowed with potent immune defenses effective against re-growth of tumor. Furthermore, LEFCT-EC with taxol was shown to be superior to conventional surgery for treatment of animals bearing melanoma tumors. As well these results surprisingly indicate that the mixture of oleum ricini with ethanol used as a taxol solvent itself in combination with LEFs has a very strong anti melanoma effect. Thus, the method of the present invention is clearly superior to all prior art methods of treating melanoma.

Example 3

Tumor Growth Retardation, Cure and Induction of Anti Tumor Immunity in Breast Carcinoma Bearing Mice Following Low-strength Electric Field Enhanced Cancer Chemotherapy Breast cancer, a frequently lethal and highly debilitating disease, is the most common cancer in the Western world, affecting about one woman in nine. To date, however, no satisfactory treatments are available for this widespread disease. Since it has previously been demonstrated that treatment of cells with LEFs has the capacity to lead to efficient cellular uptake of macromolecules, the capacity of LEF treatment to enhance uptake of chemotherapeutic agents by mammary carcinoma cells, thereby potentiating their cytotoxic activity against such cells, was demonstrated as follows.

Materials and Methods:

Animals: BALB/c female mice between the ages of 8 to 12 weeks obtained from the breeding colony of Tel-Aviv University, Israel were used in vivo tumor therapy experiments. Animal care and experimentation was carried out in accordance with Tel-Aviv University guidelines.

Tumor cell line: The highly metastatic, poorly immunogenic mammary adenocarcinoma cell line DA3 (Lopez D M. et al., 1981. J Natl Cancer Inst. 66:191) was used to generate mammary carcinoma tumors in mice. Cells were grown in DMEM supplemented with 100 U/ml penicillin, 100 µg/ml streptomycin, 4 mM glutamine, 1 mM sodium pyruvate, 1% non-essential amino acids and 10% heat-inactivated fetal calf serum (FCS), and cultured at 37° C. in a humidified incubator in an atmosphere of 7% carbon dioxide and 93% air. Tumors of this cell line grown to 1 cm in diameter produce metastatic cells, mainly in the lungs.

Reagents: Taxol (Mead Johnson Oncology Products, A Bristol-Myers Squibb, USA), obtained as a sterile nonpyrogenic solution containing 6 mg/ml paclitaxel, 527 mg/ml of purified Cremophor EL (polyoxyethylated castor oil) and 49.7% (v/v) dehydrated ethanol; and bleomycin (MegaPharm, Israel) were the anti cancer drugs used.

Other reagents used were: eosin alcoholic with methanol (Pioneer Research Chemicals, UK), Harris's haematoxylin (Pioneer Research Chemicals, UK), buffer formaldehyde (Frutarom, Israel)

Antibodies: The following FITC conjugated antibodies were employed for FACS analysis: anti-CD3 (#600F, IQP), anti-CD4 (#601F, IQP), anti-CD8a (#602F, IQP) and anti-CD19 (#604F, IQP).

Low-strength electric field enhanced cancer chemotherapy protocol: Mice were subjected to a single treatment of LEF-chemotherapy, once primary tumors reached 5 mm in diameter (about 60-70 mm$^3$) (11-17 days following subcutaneous tumor cell inoculation). Up to 100 µl of chemotherapeutic agents was injected into the tumor loci. The exposure to electric field was carried out as described above in Example 2 of the Examples section.

Anesthesia: Performed as described above in Example 2 of the Examples section.

Statistical analysis: Performed as described above in Example 2 of the Examples section.

Figure 20:
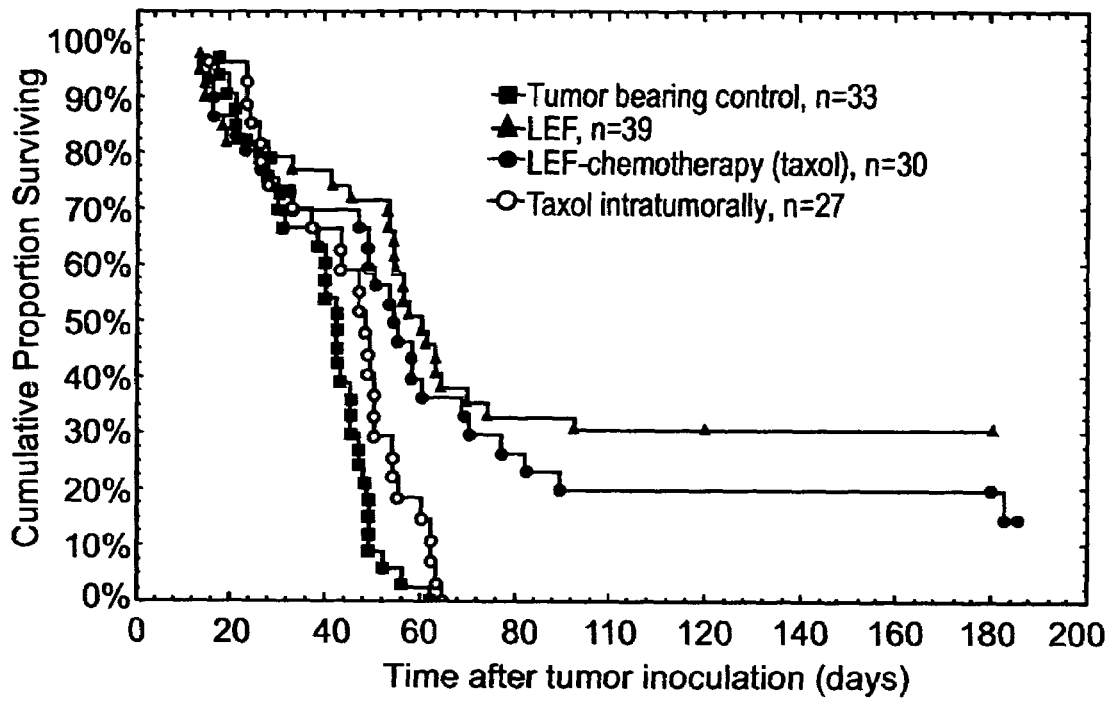
FIG. 20 is a data plot depicting the cumulative survival of DA3 mammary adenocarcinoma bearing BALB/c mice following treatment via LEF alone or treatment via LEF with taxol.
Figure 21:
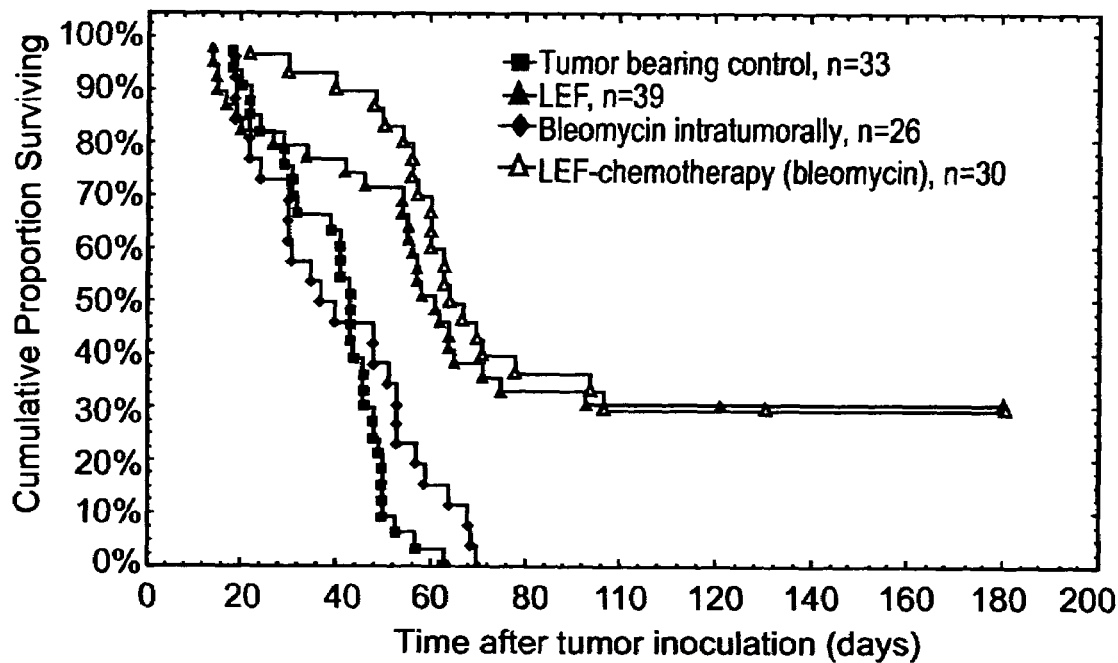
FIG. 21 is a data plot depicting the cumulative survival of DA3 mammary adenocarcinoma bearing BALB/c mice following treatment via LEF-chemotherapy alone or with bleomycin.

Experimental Results:

Effect of LEFCT-EC using bleomycin or taxol on the survival of DA3 mammary adenocarcinoma bearing nice: BALB/c mice bearing DA3 mammary adenocarcinoma were treated by LEF-chemotherapy with intratumoral taxol (20 mg/kg) (FIG. 19) or bleomycin (30 U/kg) (FIG. 20) administration and their survival rate was compared with that of mice treated only with LEF or chemotherapy. The cure rates of tumor bearing mice 180 days after tumor inoculation via LEF-chemotherapy with taxol, LEF-chemotherapy with bleomycin, and LEF alone were: 17% (FIG. 20), 30%, (FIG. 20) and 30% (FIGS. 20-21), respectively. Mantel-Cox test (comparison of groups) showed: taxol intratumorally versus LEF-chemotherapy with taxol, P=0.00593; taxol intratumorally versus tumor bearing control, P=0.01623; bleomycin intratumorally versus tumor bearing control, P=0.11113; bleomycin intratumorally versus taxol intratumorally, P=0.81751; bleomycin intratumorally versus LEF-chemotherapy with bleomycin, P<0.000004 (Table 2).

TABLE 2

Statistical comparison of survival times following treatment with LEF-chemotherapy with bleomycin, LEF-chemotherapy with taxol and LEF alone

| Treatment | Median | Mean | Std. Dv. | No. uncsd | N. censrd | Total No. |
|---|---|---|---|---|---|---|
| TB-control | 42 | 38.7 | 11.9 | 33 | 0 | 33 |
| LEF | 60 | 73.3 | 47.8 | 27 | 12 | 39 |
| Bleomycin (intratumoral) | 37.5 | 40.2 | 17.4 | 26 | 0 | 26 |
| LEF-chemotherapy with bleomycin | 64.5 | 85.3 | 45.3 | 21 | 9 | 30 |
| Taxol (intratumoral) | 48 | 43.9 | 14.4 | 27 | 0 | 27 |
| LEF-chemotherapy with taxol | 54.5 | 73.8 | 59.0 | 25 | 5 | 30 |

Figure 22:
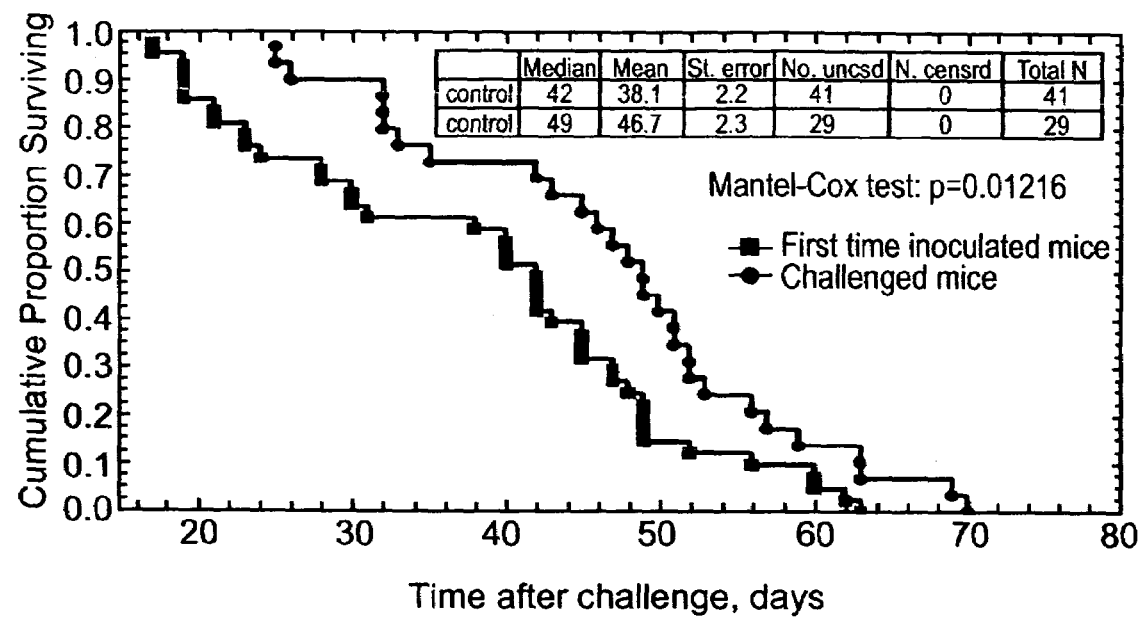
FIG. 22 is a data plot depicting the cumulative survival of BALB/c mice previously cured of DA3 mammary adenocarcinoma via LEFCT-EC treatment with taxol and subsequently challenged with a tumorigenic dose of DA3 cells. The inset table is a statistical analysis of the results shown in the data plot.

Effect of curative LEFCT-EC treatment with taxol on generation of anti DA3 tumor resistance: The resistance of mice previously cured of DA3 mammary carcinoma via LEFCT-EC treatment with taxol to tumor growth following challenge by inoculation with $10^5$ DA3 cells 120-180 days following initial tumor inoculation was analyzed. As is illustrated in FIG. 22, previously cured mice challenged with DA3 cells displayed significantly extended survival compared to first-time inoculated mice (P=0.01216). The MSTs of first-time inoculated normal mice and challenged mice were 38.1 and 46.7 days, respectively. Thus, curative treatment of DA3 tumors via LEFCT-EC treatment with taxol has the capacity to induce significant protection against growth of such a tumor in cured mice challenged with a tumorigenic dose thereof.

In order to determine whether immune effectors of cured mice possess anti DA3 activity, mice were inoculated with both a tumorigenic dose of DA3 cells as well as a dose splenocytes of previously cured mice ($10^5$ DA3 cells+$10^7$ spleen cells) (Winn assay) and the survival and tumor growth in these mice were monitored. As can be seen in Table 3, co-administration of splenocytes from LEF-chemotherapy treated mice increased the MST of inoculated animals to 39 days, as compared to 31 days in mice which received DA3 cells alone or together with splenocytes from normal mice.

TABLE 3

Effect of co-inoculation of DA3 cells with splenocytes from mice cured of DA3 tumors via LEFCT-EC treatment with taxol on tumor growth and survival

| | Mean survival time (days) | Tumor size (μl) |
|---|---|---|
| DA3 alone | 31 | 94 |
| DA3 + tumor bearing mouse splenocytes | 27 | 487 |
| DA3 + cured mouse splenocytes | 39 | 143 |
| DA3 + normal splenocytes | 31 | 97 |

The mice for Winn assay were taken 45 days after tumor inoculation.
The cells were injected in a proportion of 1:100 ($10^5$ DA3 cells + $10^7$ spleen cells) subcutaneously.
Tumor volume of the different groups was measured 14 days after inoculation.

These findings therefore demonstrate that curative treatment of mammary carcinoma in mice via LEFCT-EC with taxol leads to immune responses capable of providing resistance against re-growth of such tumors. A similar effect was also observed in mice cured by LEF without chemotherapy.

Figure 23:
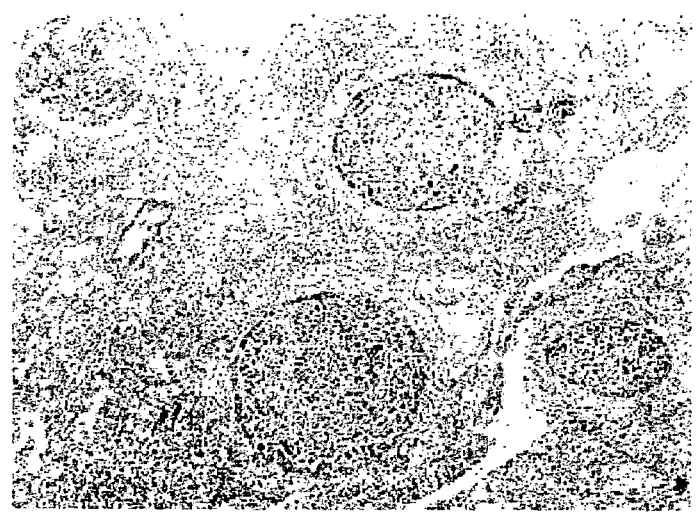
FIG. 23 is a photomicrograph depicting immune cell infiltration in pulmonary metastases of mice cured of DA3 tumors via LEFCT-EC with taxol.
Figure 24A:
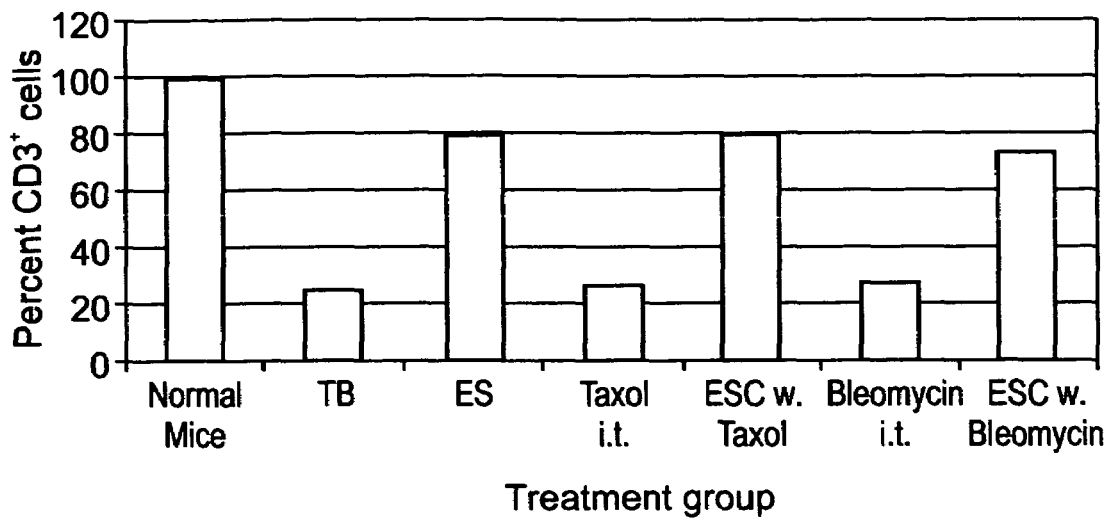
FIGS. 24*a-d* are histograms depicting a comparison of the proportions of CD3-, CD4-, CD8-, and CD19-positive splenocytes (FIGS. 24*a-d*, respectively) in normal mice, mice treated with LEF alone (ES), mice treated with intratumoral taxol injection (Taxol i.t.), mice treated via LEFCT-EC with taxol (ESC w. taxol), mice treated with intratumoral bleomycin injection (Bleomycin i.t.), and mice treated via LEFCT-EC with bleomycin (ESC w. bleomycin).
Figure 24B:
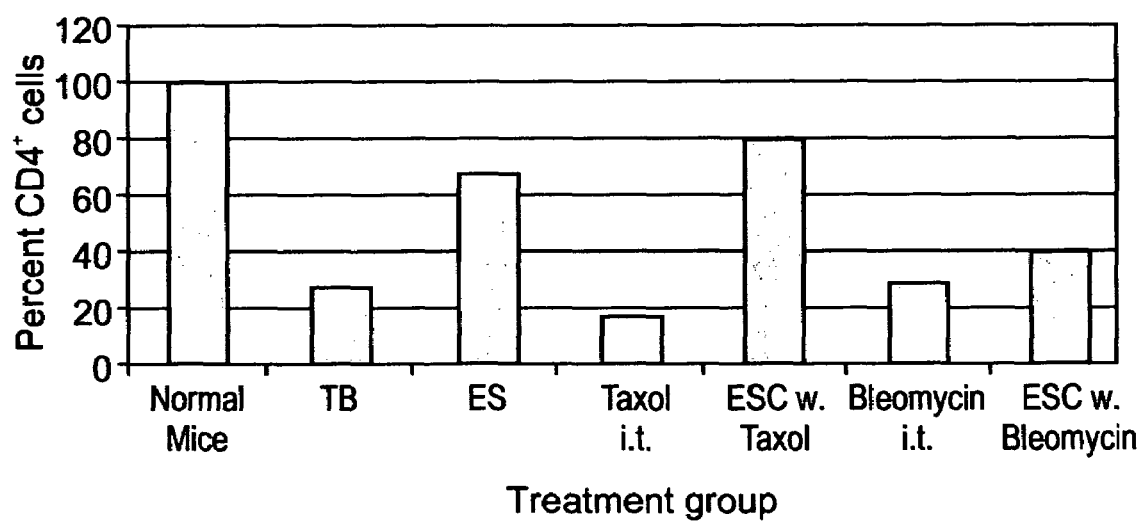
Figure 24C:
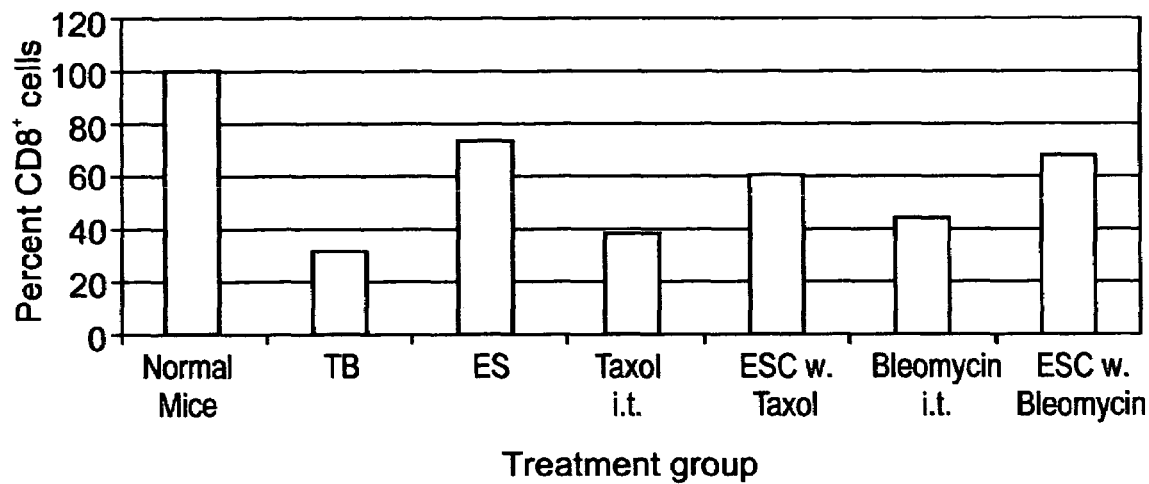
Figure 24D:
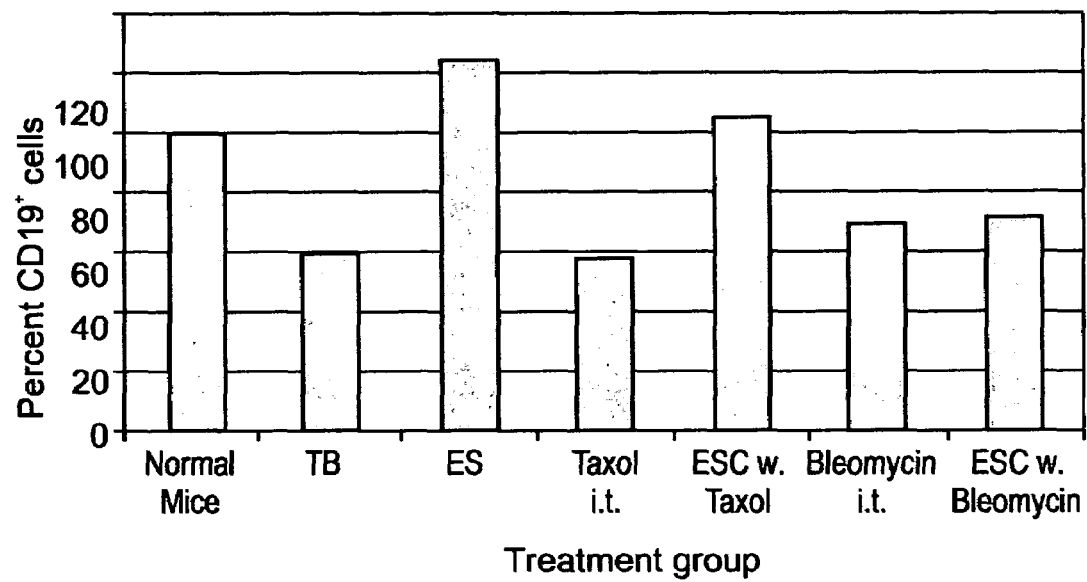

Prevention of metastasis DA3 tumors by treatment via LEFCT-EC with taxol: To examine whether mice cured of DA3 tumors via LEFCT-EC with taxol developed anti metastatic responses, the lungs of cured animals having died 2-3 months following tumor inoculation were ectomized and stained with haematoxylin and eosin. The lung metastases in untreated mice were found to have a diffuse appearance, whereas metastatic foci in LEF-chemotherapy treated mice had a pronounced capsule, comprising an immune cells infiltrate (FIG. 23). Thus, treatment of DA3 tumors via LEFCT-EC with taxol leads to an anti metastatic immune response.

Analysis of splenic lymphocyte populations in LEF and LEF-chemotherapy treated mice: In order to characterize the immunological status of DA3 tumor bearing mice following treatment via LEF, with or without taxol or bleomycin, splenocytes of treated mice (three in group) were ectomized under sterile conditions 10-12 days following the treatments (about 25 days after tumor inoculation), splenocytes were prepared, counted and one million cells were labeled with anti-CD3, anti-CD4, anti-CD8a and anti-CD19 FITC conjugated antibodies, respectively, and analyzed by FACS for surface expression of these markers. The FACS analysis showed that the proportion of CD3+(T lymphocytes), CD4+, CD8+ and CD19+(B lymphocytes) cells decreased in the tumor bearing mice and in the chemotherapy treated animals. However, mice treated via LEF with or without bleomycin or taxol were found to clearly display in all cases normal, or more normal-like splenic lymphocyte profiles of $CD3^+$, $CD4^+$, $CD8^+$, and CD19 cells than untreated tumor bearing mice (FIGS. 24a-d, respectively).

Conclusion: These results therefore demonstrate that LEFCT-EC significantly potentiates the anti mammary carcinoma activity of taxol, and that animals cured of mammary carcinomas using LEF with or without taxol are endowed with potent immune defenses effective against re-growth of tumor. Furthermore, LEFCT-EC with taxol was shown to be specifically active against metastasis of mammary carcinoma, the most frequent cause of death in patients afflicted with cancer. Also, the results presented strongly indicate that LEFCT-EC can directly destroy the primary tumors, and facilitates the destruction of residual metastatic disease by eliciting an anti tumoral immune/inflammatory response. Thus, the method of the present invention is clearly superior to all prior art methods of treating mammary carcinoma.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating an individual having a neoplastic pathology comprising applying to cells of a tumor electrical field pulses having a strength of 2-150 V/cm, a repetition frequency of 1 Hz-100 kHz and a pulse width of 1 μs-100 ms for a time period of at least 6 minutes thereby treating the individual suffering from a neoplastic disorder.

2. The method of claim 1, wherein said electrical field pulses are unipolar and are of a strength of 10-70 V/cm, a repetition frequency of 100 Hz-10 kHz and a pulse width of 1-200 μs.

3. The method of claim 1, further comprising exposing said cells of the tumor to a cytotoxic agent concomitant or prior to application of said electrical field pulses.

4. The method of claim 3, wherein said exposing said cells of the tumor to said cytotoxic agent is effected 0.1-20 minutes prior to said application of said electrical field pulses.

5. The method of claim 3, wherein said electrical field pulses are unipolar and are of a strength of 10-40 V/cm a repetition frequency of 300-2000 Hz and a pulse width of 1-200 μs.

6. The method of claim 3, wherein said exposing said cells of the tumor to said cytotoxic agent is effected by administering said cytotoxic agent to the individual.

7. The method of claim 6, wherein said administering is effected by directly injecting said cytotoxic agent into or around the tumor.

8. The method of claim 3, wherein said cytotoxic agent is selected from the group consisting of bleomycin, 5-fluorouracil, cisplatin, taxol, doxorubicin, cyclophosphamide, methotraxate and carmustine.

9. The method of claim 3, wherein said cytotoxic agent is provided in a carrier mixture including oleum ricini and ethanol.

10. The method of claim 1, further comprising determining a volume of the tumor, said volume being for determining said strength, repetition frequency and said pulse of said electrical field pulses applied to said cells of the tumor.

11. The method of claim 1, wherein said applying to cells of the tumor said electrical field pulses is effected in the absence of a cytotoxic agent.

12. The method of claim 1, wherein the neoplastic pathology is a sarcoma or carcinoma, selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma and neuroblastoma.

* * * * *